(12) United States Patent
Purdy et al.

(10) Patent No.: US 11,752,152 B1
(45) Date of Patent: Sep. 12, 2023

(54) PHARMACEUTICAL FORMULATIONS OF IMATINIB AND USES THEREOF

(71) Applicant: Exvastat Ltd, Huntingdon (GB)

(72) Inventors: Keith Purdy, Huntingdon (GB); David Cavalla, Huntingdon (GB)

(73) Assignee: Exvastat Ltd, Huntingdon (GB)

( * ) Notice: Subject to any disclaimer, the term of this patent is extended or adjusted under 35 U.S.C. 154(b) by 0 days.

(21) Appl. No.: 17/850,322

(22) Filed: Jun. 27, 2022

Related U.S. Application Data

(60) Provisional application No. 63/334,435, filed on Apr. 25, 2022.

(51) Int. Cl.
*A61K 31/506* (2006.01)
*A61K 47/08* (2006.01)
*A61K 47/10* (2017.01)

(52) U.S. Cl.
CPC ............ *A61K 31/506* (2013.01); *A61K 47/08* (2013.01); *A61K 47/10* (2013.01)

(58) Field of Classification Search
CPC ....... A61K 31/506; A61K 47/08; A61K 47/10
USPC ...................................................... 514/275
See application file for complete search history.

(56) References Cited

U.S. PATENT DOCUMENTS 9,290,765 B2   3/2016   Van Nieuw Amerongen et al.

OTHER PUBLICATIONS

Atmowihardjo et al Trials, 2022, 23:158, pp. 1-17 (Year: 2022).*
"A Ramdomized Study to Investigate the Effect of Intravenous Imatinib on the Amount of Oxygen in the Lungs and Blood of Adults with COVID-19 Needing Mechanical Ventilation and Supportive Cate. (Impress Covid)," U.S. National Library of Medicine, ClinicalTrials.gov Identifier: NCT04953052, First Posted: Jul. 7, 2021, 10 pages.
Peng et al., "Absolute Bioavailability of Imatinib (Glivec®) Orally versus Intravenous Infusion," The Journal of Clinical Pharmacology, Feb. 2004, 44(2), pp. 158-162.

* cited by examiner

*Primary Examiner* — Yevgeny Valenrod
(74) *Attorney, Agent, or Firm* — COOLEY LLP; Ivor R. Elrifi; Chen Chen

(57) ABSTRACT

The present disclosure relates to pharmaceutical formulations comprising imatinib or a pharmaceutically acceptable salt thereof. The present disclosure also relates to methods of treating or preventing a disease using the formulations.

18 Claims, No Drawings

PHARMACEUTICAL FORMULATIONS OF IMATINIB AND USES THEREOF

CROSS REFERENCE TO RELATED APPLICATION

This application claims priority to and the benefit of U.S. Provisional Application No. 63/334,435, filed on Apr. 25, 2022, the contents of which are hereby incorporated by reference in their entirety.

BACKGROUND

Imatinib is a potent small molecule tyrosine-protein kinase inhibitor originally developed for the treatment of chronic myelogenous leukemia (CML). Imatinib mesylate (Gleevec©/Glivec©) was first approved in 2001 and has been used extensively as an oral therapy to treat malignancies. Imatinib binds competitively to the ATP-binding pocket in the activation loop of ABL1, ABL2 and other receptor tyrosine kinases including PDGFR, DDR-1 and KIT, whose activity is also inhibited by imatinib.

Imatinib has been shown to protect the endothelial barrier, prevent vascular leak and reduce inflammation in a variety of animal models of sepsis, acute lung injury and impaired microcirculatory perfusion. A growing number of clinical case reports indicate imatinib has protective effects on vascular leak. Together these data suggest that imatinib may constitute promise as a novel and highly effective intervention for inflammatory vascular leak syndromes.

Acute Respiratory Distress Syndrome (ARDS) is a serious and often life-threatening condition, characterized by acute respiratory failure. Hospital mortality from ARDS is 35-45%, while ARDS survivorship carries a significant morbidity burden. Patients with ARDS have prolonged hospital admissions, and frequently develop life-threatening nosocomial infections. The COVID-19 pandemic has seen a surge of patients with ARDS in intensive care units worldwide. Around 5% of patients affected by COVID-19 require intensive care unit (ICU) admission due to ARDS, with a case-fatality rate ranging between 30 and 60%.

There are no approved pharmacological therapies for ARDS. Few therapies have attempted to target endothelial barrier dysfunction, the important common pathway in the development of ARDS. Further, a solid oral dose form (film-covered tablets) is not suitable for patients receiving mechanical ventilation. Decreased gastrointestinal perfusion can cause gastrointestinal dysfunction and may result in poor absorption of enterally administered medication. Administration of the medication by intravenous solution is thus more preferable, when treating patients with ARDS who are receiving mechanical ventilation. An intravenous solution is required to have excellent solubility, stability, sterility and possess pharmaceutical and physiological compatibility. However, in aqueous solutions imatinib mesylate was found to suffer from quick degradation under various pH at ambient temperature (J Pharm Bioall Sci 2013, 5:49-52). The present disclosure describes intravenous solutions of imatinib that address the above mentioned requirements, including stability in the aqueous solution.

SUMMARY

In some aspects, the present disclosure provides a formulation comprising Compound A:

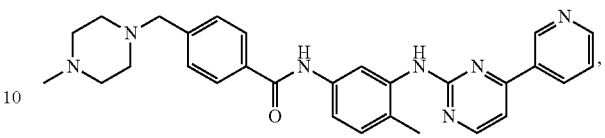

or a pharmaceutically acceptable salt thereof.

In some aspects, the present disclosure provides a method of treating or preventing a disease, comprising administering to a subject in need thereof a formulation described herein.

In some aspects, the present disclosure provides a formulation described herein for use in treating or preventing a disease in a subject in need thereof.

Unless otherwise defined, all technical and scientific terms used herein have the same meaning as commonly understood by one of ordinary skill in the art to which this disclosure belongs. In the specification, the singular forms also include the plural unless the context clearly dictates otherwise. Although methods and materials similar or equivalent to those described herein can be used in the practice or testing of the present disclosure, suitable methods and materials are described below. All publications, patent applications, patents and other references mentioned herein are incorporated by reference. The references cited herein are not admitted to be prior art to the claimed invention. In the case of conflict, the present specification, including definitions, will control. In addition, the materials, methods and examples are illustrative only and are not intended to be limiting. In the case of conflict between the chemical structures and names of the compounds disclosed herein, the chemical structures will control.

Other features and advantages of the disclosure will be apparent from the following detailed description and claims.

DETAILED DESCRIPTION

The discovery and development of a pharmaceutical formulation for intravenous infusion presents various challenges, including, but not limited to, stability and solubility of the formulation. An ideal pharmaceutical formulation for intravenous administration typically has a stable pH value, reduced impurities, and stable tonicity to maintain isotonicity. For clarity, an impurity is to be understood as a substance different from the active ingredient that is produced either in the original synthetic method, or as a result of degradation.

The present disclosure is based at least in part on a discovery that, with the components (for example, but not limited to, tonicity adjusting agents, buffering agents, and pH adjusting agents) and/or concentrations described herein, a pharmaceutical formulation of Compound A:

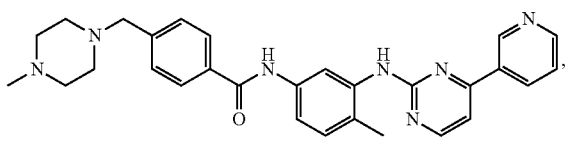 [SMILES: Cc1ccc(NC(=O)c2ccc(CN3CCN(C)CC3)cc2)cc1Nc1nccc(-c2cccnc2)n1]

or a pharmaceutically acceptable salt thereof, possesses some or all of the desired properties of the pharmaceutical formulation for intravenous administration. For example, the components described herein (e.g., tonicity adjusting agents, buffering agents, and pH adjusting agents) and/or concentrations described herein, enhances stability and solubility of Compound A, or the pharmaceutically acceptable salt thereof, in the pharmaceutical formulation for intravenous infusion. The components described herein (e.g., tonicity adjusting agents, buffering agents, and pH adjusting agents) and/or concentrations described herein, also allows the pharmaceutical formulation of Compound A, or the pharmaceutically acceptable salt thereof, to exhibit a stable pH value, reduced impurities (for example, particularly acid hydrolysis and oxidation related impurities), and stable tonicity to maintain isotonicity. Such discoveries could allow the pharmaceutical formulations described herein to be beneficial in the treatment of diseases or disorders (e.g., acute respiratory distress syndrome (ARDS) and diseases or disorders associated with pneumonia (including COVID-19 pneumonia)).

The present disclosure is based at least in part on a discovery that a formulation comprising Compound A or a pharmaceutically acceptable salt thereof present in the amount from about 7 mg/mL to about 20 mg/mL and having one or more advantageous features may be achieved by including the suitable ingredients in the formulation of the present disclosure.

The present disclosure comprises at least Compound A or its pharmaceutically acceptable salts present in the amount from about 7 mg/mL to about 20 mg/mL in combination with a tonicity adjusting agent(s), a buffering agent(s), and a pH adjusting agent(s) formulated into a pharmaceutical solution.

In some embodiments, the advantageous feature comprises: a stable pH value, reduced impurities (e.g., particularly acid hydrolysis and oxidation related impurities), and/or stable tonicity to maintain isotonicity.

Formulations of the Present Disclosure

In some aspects, the present disclosure provides a pharmaceutical formulation for intravenous administration comprising: (a) Compound A or a pharmaceutically acceptable salt thereof present in the amount from about 7 mg/mL to about 20 mg/mL; (b) a tonicity adjusting agent; (c) a buffering agent; and (d) a pH adjusting agent.

Compound A and Pharmaceutically Acceptable Salts Thereof

Compound A has the following structure:

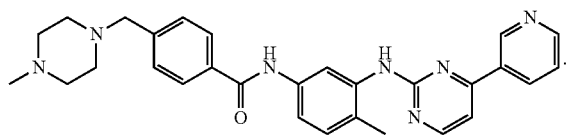 [SMILES: Cc1ccc(NC(=O)c2ccc(CN3CCN(C)CC3)cc2)cc1Nc1nccc(-c2cccnc2)n1]

(Compound A)

Compound A may also be identified by the IUPAC name of 4-[(4-methylpiperazin-1-yl)methyl]-N-[4-methyl-3-[(4-pyridin-3-ylpyrimidin-2-yl)amino]phenyl]benzamide, and may be identified by CAS No. 152459-95-5.

In some embodiments, the formulation comprises Compound A.

In some embodiments, the formulation comprises a pharmaceutically acceptable salt of Compound A.

In some embodiments, the formulation comprises a mesylate salt of Compound A (i.e., imatinib mesylate).

The mesylate salt of Compound A (i.e., imatinib mesylate) has the following structure:

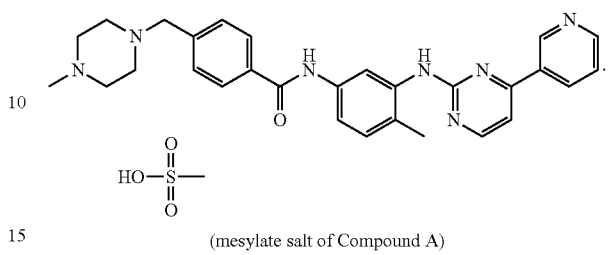

(mesylate salt of Compound A)

The mesylate salt of Compound A may also be identified by the IUPAC name of 4-[(4-methylpiperazin-1-yl)methyl]-N-(4-methyl-3-[[4-(pyridin-3-yl)pyrimidin yl]amino]phenyl)benzamide methanesulfonate, and may be identified by CAS No. 220127-57-1.

In some embodiments, Compound A or a pharmaceutically acceptable salt thereof is present in the formulation in the amount from about 7 mg/mL to about 20 mg/mL, from about 7 mg/mL to about 19 mg/mL, from about 7 mg/mL to about 18 mg/mL, from about 7 mg/mL to about 17 mg/mL, from about 7 mg/mL to about 16 mg/mL, from about 7 mg/mL to about 15 mg/mL, from about 7 mg/mL to about 14 mg/mL, from about 7 mg/mL to about 14 mg/mL, from about 7 mg/mL to about 12 mg/mL, from about 7 mg/mL to about 11 mg/mL, from about 7 mg/mL to about 10 mg/mL, from about 7 mg/mL to about 9 mg/mL, from about 7.1 mg/mL to about 8.9 mg/mL, from about 7.2 mg/mL to about 8.8 mg/mL, from about 7.3 mg/mL to about 8.7 mg/mL, from about 7.4 mg/mL to about 8.6 mg/mL, from about 7.5 mg/mL to about 8.5 mg/mL, or from about 7.6 mg/mL to about 8.4 mg/mL. In some embodiments, Compound A or a pharmaceutically acceptable salt thereof is present in the formulation in the amount from about 7 mg/mL to about 9 mg/mL, from about 7.1 mg/mL to about 8.9 mg/mL, from about 7.2 mg/mL to about 8.8 mg/mL, from about 7.3 mg/mL to about 8.7 mg/mL, from about 7.4 mg/mL to about 8.6 mg/mL, from about 7.5 mg/mL to about 8.5 mg/mL, or from about 7.6 mg/mL to about 8.4 mg/mL. In some embodiments, Compound A or a pharmaceutically acceptable salt thereof is present in the formulation in the amount from about 7.4 mg/mL to about 8.6 mg/mL, from about 7.5 mg/mL to about 8.5 mg/mL, or from about 7.6 mg/mL to about 8.4 mg/mL. In some embodiments, Compound A or a pharmaceutically acceptable salt thereof is present in the formulation in the amount from about 7.6 mg/mL to about 8.4 mg/mL.

In some embodiments, Compound A or a pharmaceutically acceptable salt thereof is present in the formulation in the amount of about 6.5 mg/mL, about 6.6 mg/mL, about 6.7 mg/mL, about 6.8 mg/mL, about 6.9 mg/mL, about 7.0 mg/mL, about 7.1 mg/mL, about 7.2 mg/mL, about 7.3 mg/mL, about 7.4 mg/mL, about 7.5 mg/mL, about 7.6 mg/mL, about 7.7 mg/mL, about 7.8 mg/mL, about 7.9 mg/mL, about 8.0 mg/mL, about 8.1 mg/mL, about 8.2 mg/mL, about 8.3 mg/mL, about 8.4 mg/mL, about 8.5 mg/mL, about 8.6 mg/mL, about 8.7 mg/mL, about 8.8 mg/mL, about 8.9 mg/mL, about 9.0 mg/mL, about 9.1 mg/mL, about 9.2 mg/mL, about 9.3 mg/mL, about 9.4 mg/mL, about 9.5 mg/mL, about 9.6 mg/mL, about 9.7 mg/mL, about 9.8 mg/mL, about 9.9 mg/mL, or about 10 mg/mL. In some embodiments, Compound A or a pharmaceutically acceptable salt thereof is present in the formulation in the amount of about 7.0 mg/mL, about 7.1 mg/mL, about 7.2 mg/mL, about 7.3 mg/mL, about 7.4 mg/mL, about 7.5 mg/mL, about 7.6 mg/mL, about 7.7 mg/mL, about 7.8 mg/mL, about 7.9 mg/mL, about 8.0 mg/mL, about 8.1 mg/mL, about 8.2 mg/mL, about 8.3 mg/mL, about 8.4 mg/mL, about 8.5 mg/mL, about 8.6 mg/mL, about 8.7 mg/mL, about 8.8 mg/mL, about 8.9 mg/mL, or about 9.0 mg/mL. In some embodiments, Compound A or a pharmaceutically acceptable salt thereof is present in the formulation in the amount of about 7.4 mg/mL, about 7.5 mg/mL, about 7.6 mg/mL, about 7.7 mg/mL, about 7.8 mg/mL, about 7.9 mg/mL, about 8.0 mg/mL, about 8.1 mg/mL, about 8.2 mg/mL, about 8.3 mg/mL, about 8.4 mg/mL, about 8.5 mg/mL, or about 8.6 mg/mL. In some embodiments, Compound A or a pharmaceutically acceptable salt thereof is present in the formulation in the amount of about 7.6 mg/mL, about 7.7 mg/mL, about 7.8 mg/mL, about 7.9 mg/mL, about 8.0 mg/mL, about 8.1 mg/mL, about 8.2 mg/mL, about 8.3 mg/mL, or about 8.4 mg/mL.

In some embodiments, Compound A is present in the formulation in the amount described herein.

Tonicity Adjusting Agents

In some embodiments, the tonicity adjusting agent is selected from a saccharide (e.g., dextrose, glucose, mannitol, and sorbitol), a polyhydric alcohol (e.g., glycerol and PEG), a salt (e.g., NaCl), and a combination thereof.

In some embodiments, the tonicity adjusting agent is selected from a polyhydric alcohol (e.g., glycerol and PEG), a salt (e.g., NaCl), and a combination thereof.

In some embodiments, the tonicity adjusting agent is selected from a polyhydric alcohol (e.g., glycerol and PEG).

In some embodiments, the tonicity adjusting agent is selected from glycerol, NaCl, and a combination thereof.

In some embodiments, the tonicity adjusting agent is glycerol.

In some embodiments, the tonicity adjusting agent is present in the formulation from about 0.1% (v/v) to about 10.0% (v/v), from about 0.1% (v/v) to about 9.0% (v/v), from about 0.1% (v/v) to about 8.0% (v/v), from about 0.1% (v/v) to about 7.0% (v/v), from about 0.1% (v/v) to about 6.0% (v/v), from about 0.1% (v/v) to about 5.0% (v/v), from about 0.1% (v/v) to about 4.0% (v/v), from about 0.1% (v/v) to about 3.0% (v/v), from about 0.1% (v/v) to about 2.0% (v/v), from about 0.5% (v/v) to about 10.0% (v/v), from about 0.5% (v/v) to about 9.0% (v/v), from about 0.5% (v/v) to about 8.0% (v/v), from about 0.5% (v/v) to about 7.0% (v/v), from about 0.5% (v/v) to about 6.0% (v/v), from about 0.5% (v/v) to about 5.0% (v/v), from about 0.5% (v/v) to about 4.0% (v/v), from about 0.5% (v/v) to about 3.0% (v/v), from about 0.5% (v/v) to about 2.0% (v/v), from about 1.0% (v/v) to about 10.0% (v/v), from about 1.0% (v/v) to about 9.0% (v/v), from about 1.0% (v/v) to about 8.0% (v/v), from about 1.0% (v/v) to about 7.0% (v/v), from about 1.0% (v/v) to about 6.0% (v/v), from about 1.0% (v/v) to about 5.0% (v/v), from about 1.0% (v/v) to about 4.0% (v/v), from about 1.0% (v/v) to about 3.0% (v/v), from about 1.0% (v/v) to about 2.0% (v/v), from about 1.5% (v/v) to about 10.0% (v/v), from about 1.5% (v/v) to about 9.0% (v/v), from about 1.5% (v/v) to about 8.0% (v/v), from about 1.5% (v/v) to about 7.0% (v/v), from about 1.5% (v/v) to about 6.0% (v/v), from about 1.5% (v/v) to about 5.0% (v/v), from about 1.5% (v/v) to about 4.0% (v/v), from about 1.5% (v/v) to about 3.0% (v/v), from about 1.5% (v/v) to about 2.0% (v/v), from about 1.0% (v/v) to about 2.5% (v/v), or from about 1.5% (v/v) to about 2.5% (v/v).

In some embodiments, the tonicity adjusting agent that is glycerol is present in the formulation from about 0.1% (v/v) to about 10.0% (v/v), from about 0.1% (v/v) to about 9.0% (v/v), from about 0.1% (v/v) to about 8.0% (v/v), from about 0.1% (v/v) to about 7.0% (v/v), from about 0.1% (v/v) to about 6.0% (v/v), from about 0.1% (v/v) to about 5.0% (v/v), from about 0.1% (v/v) to about 4.0% (v/v), from about 0.1% (v/v) to about 3.0% (v/v), from about 0.1% (v/v) to about 2.0% (v/v), from about 0.5% (v/v) to about 10.0% (v/v), from about 0.5% (v/v) to about 9.0% (v/v), from about 0.5% (v/v) to about 8.0% (v/v), from about 0.5% (v/v) to about 7.0% (v/v), from about 0.5% (v/v) to about 6.0% (v/v), from about 0.5% (v/v) to about 5.0% (v/v), from about 0.5% (v/v) to about 4.0% (v/v), from about 0.5% (v/v) to about 3.0% (v/v), from about 0.5% (v/v) to about 2.0% (v/v), from about 1.0% (v/v) to about 10.0% (v/v), from about 1.0% (v/v) to about 9.0% (v/v), from about 1.0% (v/v) to about 8.0% (v/v), from about 1.0% (v/v) to about 7.0% (v/v), from about 1.0% (v/v) to about 6.0% (v/v), from about 1.0% (v/v) to about 5.0% (v/v), from about 1.0% (v/v) to about 4.0% (v/v), from about 1.0% (v/v) to about 3.0% (v/v), from about 1.0% (v/v) to about 2.0% (v/v), from about 1.5% (v/v) to about 10.0% (v/v), from about 1.5% (v/v) to about 9.0% (v/v), from about 1.5% (v/v) to about 8.0% (v/v), from about 1.5% (v/v) to about 7.0% (v/v), from about 1.5% (v/v) to about 6.0% (v/v), from about 1.5% (v/v) to about 5.0% (v/v), from about 1.5% (v/v) to about 4.0% (v/v), from about 1.5% (v/v) to about 3.0% (v/v), from about 1.5% (v/v) to about 2.0% (v/v), from about 1.0% (v/v) to about 2.5% (v/v), or from about 1.5% (v/v) to about 2.5% (v/v).

In some embodiments, the tonicity adjusting agent that is glycerol is present in the formulation of about 1.5% (v/v), about 1.6% (v/v), about 1.7% (v/v), about 1.8% (v/v), about 1.9% (v/v), about 2.0% (v/v), about 2.1% (v/v), about 2.2% (v/v), about 2.3% (v/v), about 2.4% (v/v), or about 2.5% (v/v).

In some embodiments, the tonicity adjusting agent that is glycerol is present in the formulation of about 1.9% (v/v).

Buffering Agents

In some embodiments, the buffering agent is selected from a phosphate buffer, a borate buffer, a citrate buffer, a tartrate buffer, an acetate buffer, an amino acid, and a combination thereof.

In some embodiments, the buffering agent is an acetate buffer.

In some embodiments, the buffering agent is present in the formulation at a concentration from about 0.001 M to about 0.05 M, from about 0.002 M to about 0.05 M, from about 0.003 M to about 0.05 M, from about 0.004 M to about 0.05 M, from about 0.005 M to about 0.05 M, 0.006 M to about 0.05 M, from about 0.007 M to about 0.05 M, from about 0.008 M to about 0.05 M, from about 0.009 M to about 0.05 M, from about 0.01 M to about 0.05 M, from about 0.001 M to about 0.04 M, from about 0.002 M to about 0.04 M, from about 0.003 M to about 0.04 M, from about 0.004 M to about 0.04 M, from about 0.005 M to about 0.04 M, 0.006 M to about 0.04 M, from about 0.007 M to about 0.04 M, from about 0.008 M to about 0.04 M, from about 0.009 M to about 0.04 M, from about 0.01 M to about 0.04 M, from about 0.001 M to about 0.03 M, from about 0.002 M to about 0.03 M, from about 0.003 M to about 0.03 M, from about 0.004 M to about 0.03 M, from about 0.005 M to about 0.03 M, 0.006 M to about 0.03 M, from about 0.007 M to about 0.03 M, from about 0.008 M to about 0.03 M, from about 0.009 M to about 0.03 M, from about 0.01 M to about 0.03 M, from about 0.001 M to about 0.02 M, from about 0.002 M to about 0.02 M, from about 0.003 M to about 0.02 M, from about 0.004 M to about 0.02 M, from about 0.005 M to about 0.02 M, 0.006 M to about 0.02 M, from about 0.007 M to about 0.02 M, from about 0.008 M to about 0.02 M, from about 0.009 M to about 0.02 M, from about 0.01 M to about 0.02 M, from about 0.001 M to about 0.015 M, from about 0.002 M to about 0.015 M, from about 0.003 M to about 0.015 M, from about 0.004 M to about 0.015 M, from about 0.005 M to about 0.015 M, 0.006 M to about 0.015 M, from about 0.007 M to about 0.015 M, from about 0.008 M to about 0.015 M, from about 0.009 M to about 0.015 M, or from about 0.01 M to about 0.015 M.

In some embodiments, the buffering agent that is an acetate buffer is present in the formulation at a concentration from about 0.001 M to about 0.05 M, from about 0.002 M to about 0.05 M, from about 0.003 M to about 0.05 M, from about 0.004 M to about 0.05 M, from about 0.005 M to about 0.05 M, 0.006 M to about 0.05 M, from about 0.007 M to about 0.05 M, from about 0.008 M to about 0.05 M, from about 0.009 M to about 0.05 M, from about 0.01 M to about 0.05 M, from about 0.001 M to about 0.04 M, from about 0.002 M to about 0.04 M, from about 0.003 M to about 0.04 M, from about 0.004 M to about 0.04 M, from about 0.005 M to about 0.04 M, 0.006 M to about 0.04 M, from about 0.007 M to about 0.04 M, from about 0.008 M to about 0.04 M, from about 0.009 M to about 0.04 M, from about 0.01 M to about 0.04 M, from about 0.001 M to about 0.03 M, from about 0.002 M to about 0.03 M, from about 0.003 M to about 0.03 M, from about 0.004 M to about 0.03 M, from about 0.005 M to about 0.03 M, 0.006 M to about 0.03 M, from about 0.007 M to about 0.03 M, from about 0.008 M to about 0.03 M, from about 0.009 M to about 0.03 M, from about 0.01 M to about 0.03 M, from about 0.001 M to about 0.02 M, from about 0.002 M to about 0.02 M, from about 0.003 M to about 0.02 M, from about 0.004 M to about 0.02 M, from about 0.005 M to about 0.02 M, 0.006 M to about 0.02 M, from about 0.007 M to about 0.02 M, from about 0.008 M to about 0.02 M, from about 0.009 M to about 0.02 M, from about 0.01 M to about 0.02 M, from about 0.001 M to about 0.015 M, from about 0.002 M to about 0.015 M, from about 0.003 M to about 0.015 M, from about 0.004 M to about 0.015 M, from about 0.005 M to about 0.015 M, 0.006 M to about 0.015 M, from about 0.007 M to about 0.015 M, from about 0.008 M to about 0.015 M, from about 0.009 M to about 0.015 M, or from about 0.01 M to about 0.015 M.

In some embodiments, the buffering agent that is an acetate buffer is present in the formulation at a concentration of about 0.01 M.

pH Adjusting Agents

In some embodiments, a pH adjusting agent may be needed to maintain a desired pH range.

In some embodiments, the formulation pH is adjusted using a weak base. In some embodiments, the formulation pH is adjusted using a dilute base. In some embodiments, the formulation pH is adjusted using a strong base. In some embodiments, the formulation pH is adjusted using a weak and dilute base. In some embodiments, the formulation pH is adjusted using a strong and dilute base. In some embodiments, the formulation pH is adjusted using NaOH. In some embodiments, the formulation pH is adjusted using KOH. In some embodiments, the formulation pH is adjusted using 1N NaOH. In some embodiments, the formulation pH is adjusted using 1N KOH. In some embodiments, the formulation pH is adjusted using 0.5N NaOH. In some embodiments, the formulation pH is adjusted using 0.5N KOH.

In some embodiments, the pH adjusting agent is in sufficient quantity for pH adjustment from 4.5 to 5.5, from 4.5 to 4.9, from 5.0 to 5.2, or from 5.3 to 5.5.

In some embodiments, the pH adjusting agent is in sufficient quantity for pH adjustment to 4.8, 4.9, 5.0, 5.1, 5.2, or 5.3.

In some embodiments, the pH adjusting agent comprises NaOH aqueous solution in sufficient quantity for pH adjustment from 4.5 to 5.5, from 4.5 to 4.9, from 5.0 to 5.2, or from 5.3 to 5.5.

In some embodiments, the pH adjusting agent comprises NaOH aqueous solution in sufficient quantity for pH adjustment to 4.8, 4.9, 5.0, 5.1, 5.2, or 5.3.

In some embodiments, the formulation pH is adjusted using a weak acid. In some embodiments, the formulation pH is adjusted using a dilute acid. In some embodiments, the formulation pH is adjusted using a strong acid. In some embodiments, the formulation pH is adjusted using a weak and dilute acid. In some embodiments, the formulation pH is adjusted using a strong and dilute acid. In some embodiments, the formulation pH is adjusted using hydrochloric acid. In some embodiments, the formulation pH is adjusted using 1N hydrochloric acid. In some embodiments, the formulation pH is adjusted using 0.5N hydrochloric acid.

In some embodiments, the pH adjusting agent comprises hydrochloric acid in sufficient quantity for pH adjustment from 4.5 to 5.5, from 4.5 to 4.9, from 5.0 to 5.2, or from 5.3 to 5.5.

In some embodiments, the pH adjusting agent comprises hydrochloric acid in sufficient quantity for pH adjustment to 4.8, 4.9, 5.0, 5.1, 5.2, or 5.3.

Impurities

In some embodiments, the formulation is substantially pure, i.e., essentially free of impurities. In some embodiments, the formulation comprises impurities below in an amount described herein.

In some embodiments, the formulation comprises Impurity F:

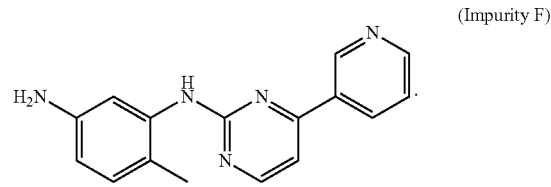 [SMILES: Cc1ccc(N)cc1Nc1nccc(-c2cccnc2)n1]

(Impurity F)

Impurity F may also be identified by the IUPAC name of 4-methyl-N3-[4-(pyridin-3-yl)pyrimidin-2-yl]benzene-1,3-diamine, and may be identified by CAS No. 152460-10-1.

In some embodiments, the formulation comprises Impurity J:

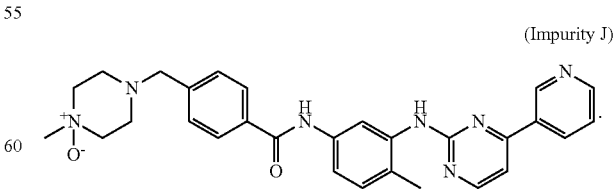

(Impurity J)

Impurity J may also be identified by the IUPAC name of 4-((4-methyl-4-oxidopiperazin-1-yl)methyl)-N-[4-methyl-3-[[4-(pyridin-3-yl)pyrimidin-2-yl]amino)phenyl]benzamide, and may be identified by CAS No. 938082-57-6.

In some embodiments, the formulation comprises Impurity A:

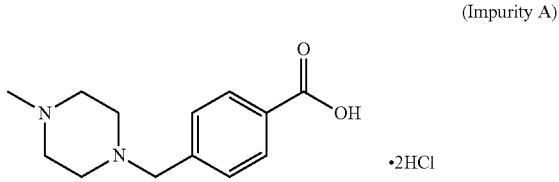 [SMILES: CN1CCN(Cc2ccc(C(=O)O)cc2)CC1]
(Impurity A)

Impurity A may also be identified by the IUPAC name of 4-[(4-methyl-1-piperazinyl)methyl]benzoic acid dihydrochloride, and may be identified by CAS No. 106261-49-8.

It is understood that Impurity A may also be referred to as CAPB herein.

In some embodiments, the formulation comprises Impurity B:

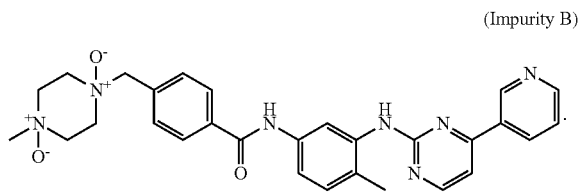 [SMILES: Cc1ccc(NC(=O)c2ccc(C[N+]3([O-])CC[N+](C)([O-])CC3)cc2)cc1Nc1nccc(-c2cccnc2)n1]
(Impurity B)

Impurity B may also be identified by the IUPAC name of 4-[(4-methyl-1,4-dioxidopiperazine-1,4-diium-1-yl) methyl]-N-[4-methyl-3-[(4-pyridin-3-ylpyrimidin yl)amino]phenyl]benzamide, and may be identified by CAS No. 571186-93-1.

It is understood that Impurity B may also be referred to as RRT 0.66 or degradation product RRT 0.66 herein.

In some embodiments, the formulation comprises Impurity C:

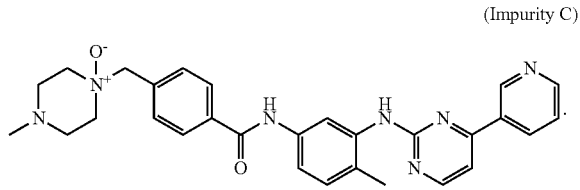 [SMILES: Cc1ccc(NC(=O)c2ccc(C[N+]3([O-])CCN(C)CC3)cc2)cc1Nc1nccc(-c2cccnc2)n1]
(Impurity C)

Impurity C may also be identified by the IUPAC name of 4-[(4-methyl-1-oxidopiperazin-1-ium-1-yl)methyl]-N-[4-methyl-3-[(4-pyridin-3-ylpyrimidin-2-yl)amino]phenyl] benzamide, and may be identified by CAS No. 938082-57-6.

It is understood that Impurity C may also be referred to as RRT 0.71 or degradation product RRT 0.71 herein.

In some embodiments, the formulation comprises about 5% w/w or less, about 4.5% w/w or less, about 4% w/w or less, about 3.5% w/w or less, about 3% w/w or less, about 2.5% w/w or less, about 2% w/w or less, about 1.5% w/w or less, about 1.0% w/w or less, about 0.9% w/w or less, about 0.8% w/w or less, about 0.7% w/w or less, about 0.6% w/w or less, about 0.5% w/w or less, about 0.4% w/w or less, about 0.3% w/w or less, about 0.2% w/w or less, about 0.1% w/w or less, about 0.09% w/w or less, about 0.08% w/w or less, about 0.07% w/w or less, about 0.06% w/w or less, about 0.05% w/w or less, about 0.04% w/w or less, about 0.03% w/w or less, about 0.02% w/w or less, or about 0.01% w/w or less of one or more impurities (e.g., Impurity F, Impurity J, Impurity A, Impurity B, and/or Impurity C).

In some embodiments, the formulation comprises about 5% w/w or less, about 4.5% w/w or less, about 4% w/w or less, about 3.5% w/w or less, about 3% w/w or less, about 2.5% w/w or less, about 2% w/w or less, about 1.5% w/w or less, about 1% w/w or less, about 0.9% w/w or less, about 0.8% w/w or less, about 0.7% w/w or less, about 0.6% w/w or less, about 0.5% w/w or less, about 0.4% w/w or less, about 0.3% w/w or less, about 0.2% w/w or less, about 0.1% w/w or less, about 0.09% w/w or less, about 0.08% w/w or less, about 0.07% w/w or less, about 0.06% w/w or less, about 0.05% w/w or less, about 0.04% w/w or less, about 0.03% w/w or less, about 0.02% w/w or less, or about 0.01% w/w or less of one or more impurities (e.g., Impurity F, Impurity J, Impurity A, Impurity B, and/or Impurity C) upon storage for an extended period (e.g., at least two weeks, at least three weeks, at least four weeks, at least six weeks, at least two months, at least four months, at least six months, at least twelve months, at least eighteen months, or at least two years), under various temperature (e.g., about 25° C., about 30° C., about 35° C., or about 40° C.) and humidity (e.g., about 40% RH (relative humidity), about 45% RH, about 50% RH, about 55% RH, about 60% RH, about 65% RH, about 70% RH, about 75% RH, about 80% RH, about 85% RH, or about 90% RH).

In some embodiments, the formulation comprises about 5% w/w or less, about 4.5% w/w or less, about 4% w/w or less, about 3.5% w/w or less, about 3% w/w or less, about 2.5% w/w or less, about 2% w/w or less, about 1.5% w/w or less, about 1% w/w or less, about 0.9% w/w or less, about 0.8% w/w or less, about 0.7% w/w or less, about 0.6% w/w or less, about 0.5% w/w or less, about 0.4% w/w or less, about 0.3% w/w or less, about 0.2% w/w or less, about 0.1% w/w or less, about 0.09% w/w or less, about 0.08% w/w or less, about 0.07% w/w or less, about 0.06% w/w or less, about 0.05% w/w or less, about 0.04% w/w or less, about 0.03% w/w or less, about 0.02% w/w or less, or about 0.01% w/w or less of one or more impurities (e.g., Impurity F, Impurity J, Impurity A, Impurity B, and/or Impurity C) upon storage at about 25° C. and about 60% RH for an extended period (e.g., at least two weeks, at least three weeks, at least four weeks, at least six weeks, at least two months, at least four months, at least six months, at least twelve months, at least eighteen months, or at least two years).

In some embodiments, the formulation comprises about 5% w/w or less, about 4.5% w/w or less, about 4% w/w or less, about 3.5% w/w or less, about 3% w/w or less, about 2.5% w/w or less, about 2% w/w or less, about 1.5% w/w or less, about 1% w/w or less, about 0.9% w/w or less, about 0.8% w/w or less, about 0.7% w/w or less, about 0.6% w/w or less, about 0.5% w/w or less, about 0.4% w/w or less, about 0.3% w/w or less, about 0.2% w/w or less, about 0.1% w/w or less, about 0.09% w/w or less, about 0.08% w/w or less, about 0.07% w/w or less, about 0.06% w/w or less, about 0.05% w/w or less, about 0.04% w/w or less, about 0.03% w/w or less, about 0.02% w/w or less, or about 0.01% w/w or less of one or more impurities (e.g., Impurity F, Impurity J, Impurity A, Impurity B, and/or Impurity C) upon storage at about 25° C. and about 60% RH for about 1 month, about 2 months, about 3, months, about 4 months, about 5 months, about 6 months, about 7 months, about 8 months, about 9 months, about 10 months, about 11 months, about 12 months, about 14 months, about 16 months, about 18 months, about 20 months, about 22 months, about 24 months, about 26 months, about 28 months, about 30 months, about 32 months, about 34 months, about 36 months, about 38 months, about 40 months, about 42 months, about 44 months, about 46 months, or about 48 months.

In some embodiments, the formulation comprises about 5% w/w or less, about 4.5% w/w or less, about 4% w/w or less, about 3.5% w/w or less, about 3% w/w or less, about 2.5% w/w or less, about 2% w/w or less, about 1.5% w/w or less, about 1% w/w or less, about 0.9% w/w or less, about 0.8% w/w or less, about 0.7% w/w or less, about 0.6% w/w or less, about 0.5% w/w or less, about 0.4% w/w or less, about 0.3% w/w or less, about 0.2% w/w or less, about 0.1% w/w or less, about 0.09% w/w or less, about 0.08% w/w or less, about 0.07% w/w or less, about 0.06% w/w or less, about 0.05% w/w or less, about 0.04% w/w or less, about 0.03% w/w or less, about 0.02% w/w or less, or about 0.01% w/w or less of one or more impurities (e.g., Impurity F, Impurity J, Impurity A, Impurity B, and/or Impurity C) upon storage at about 40° C. and about 75% RH for an extended period (e.g., at least two weeks, at least three weeks, at least four weeks, at least six weeks, at least two months, at least four months, at least six months, at least twelve months, at least eighteen months, or at least two years).

In some embodiments, the formulation comprises about 5% w/w or less, about 4.5% w/w or less, about 4% w/w or less, about 3.5% w/w or less, about 3% w/w or less, about 2.5% w/w or less, about 2% w/w or less, about 1.5% w/w or less, about 1% w/w or less, about 0.9% w/w or less, about 0.8% w/w or less, about 0.7% w/w or less, about 0.6% w/w or less, about 0.5% w/w or less, about 0.4% w/w or less, about 0.3% w/w or less, about 0.2% w/w or less, about 0.1% w/w or less, about 0.09% w/w or less, about 0.08% w/w or less, about 0.07% w/w or less, about 0.06% w/w or less, about 0.05% w/w or less, about 0.04% w/w or less, about 0.03% w/w or less, about 0.02% w/w or less, or about 0.01% w/w or less of one or more impurities (e.g., Impurity F, Impurity J, Impurity A, Impurity B, and/or Impurity C) upon storage at about 40° C. and about 75% RH for about 1 month, about 2 months, about 3, months, about 4 months, about 5 months, about 6 months, about 7 months, about 8 months, about 9 months, about 10 months, about 11 months, about 12 months, about 14 months, about 16 months, about 18 months, about 20 months, about 22 months, about 24 months, about 26 months, about 28 months, about 30 months, about 32 months, about 34 months, about 36 months, about 38 months, about 40 months, about 42 months, about 44 months, about 46 months, or about 48 months.

In some embodiments, the formulation comprises about 20% w/w or less, about 15% w/w or less, about 10% w/w or less, about 9% w/w or less, about 8% w/w or less, about 7% w/w or less, about 6% w/w or less, about 5% w/w or less, about 4.5% w/w or less, about 4% w/w or less, about 3.5% w/w or less, about 3% w/w or less, about 2.5% w/w or less, about 2% w/w or less, about 1.5% w/w or less, about 1% w/w or less, about 0.9% w/w or less, about 0.8% w/w or less, about 0.7% w/w or less, about 0.6% w/w or less, about 0.5% w/w or less, about 0.4% w/w or less, about 0.3% w/w or less, about 0.2% w/w or less, about 0.1% w/w or less, about 0.09% w/w or less, about 0.08% w/w or less, about 0.07% w/w or less, about 0.06% w/w or less, about 0.05% w/w or less, about 0.04% w/w or less, about 0.03% w/w or less, about 0.02% w/w or less, or about 0.01% w/w or less of total impurities (e.g., Impurity F, Impurity J, Impurity A, Impurity B, Impurity C, etc.).

In some embodiments, the formulation comprises about 20% w/w or less, about 15% w/w or less, about 10% w/w or less, about 9% w/w or less, about 8% w/w or less, about 7% w/w or less, about 6% w/w or less, about 5% w/w or less, about 4.5% w/w or less, about 4% w/w or less, about 3.5% w/w or less, about 3% w/w or less, about 2.5% w/w or less, about 2% w/w or less, about 1.5% w/w or less, about 1% w/w or less, about 0.9% w/w or less, about 0.8% w/w or less, about 0.7% w/w or less, about 0.6% w/w or less, about 0.5% w/w or less, about 0.4% w/w or less, about 0.3% w/w or less, about 0.2% w/w or less, about 0.1% w/w or less, about 0.09% w/w or less, about 0.08% w/w or less, about 0.07% w/w or less, about 0.06% w/w or less, about 0.05% w/w or less, about 0.04% w/w or less, about 0.03% w/w or less, about 0.02% w/w or less, or about 0.01% w/w or less of total impurities (e.g., Impurity F, Impurity J, Impurity A, Impurity B, Impurity C, etc.) upon storage at about 25° C. and about 60% RH for an extended period (e.g., at least two weeks, at least three weeks, at least four weeks, at least six weeks, at least two months, at least four months, at least six months, at least twelve months, at least eighteen months, or at least two years).

In some embodiments, the formulation comprises about 20% w/w or less, about 15% w/w or less, about 10% w/w or less, about 9% w/w or less, about 8% w/w or less, about 7% w/w or less, about 6% w/w or less, about 5% w/w or less, about 4.5% w/w or less, about 4% w/w or less, about 3.5% w/w or less, about 3% w/w or less, about 2.5% w/w or less, about 2% w/w or less, about 1.5% w/w or less, about 1% w/w or less, about 0.9% w/w or less, about 0.8% w/w or less, about 0.7% w/w or less, about 0.6% w/w or less, about 0.5% w/w or less, about 0.4% w/w or less, about 0.3% w/w or less, about 0.2% w/w or less, about 0.1% w/w or less, about 0.09% w/w or less, about 0.08% w/w or less, about 0.07% w/w or less, about 0.06% w/w or less, about 0.05% w/w or less, about 0.04% w/w or less, about 0.03% w/w or less, about 0.02% w/w or less, or about 0.01% w/w or less total impurities (e.g., Impurity F, Impurity J, Impurity A, Impurity B, Impurity C, etc.) upon storage at about 25° C. and about 60% RH for about 1 month, about 2 months, about 3, months, about 4 months, about 5 months, about 6 months, about 7 months, about 8 months, about 9 months, about 10 months, about 11 months, about 12 months, about 14 months, about 16 months, about 18 months, about 20 months, about 22 months, about 24 months, about 26 months, about 28 months, about 30 months, about 32 months, about 34 months, about 36 months, about 38 months, about 40 months, about 42 months, about 44 months, about 46 months, or about 48 months.

In some embodiments, the formulation comprises about 20% w/w or less, about 15% w/w or less, about 10% w/w or less, about 9% w/w or less, about 8% w/w or less, about 7% w/w or less, about 6% w/w or less, about 5% w/w or less, about 4.5% w/w or less, about 4% w/w or less, about 3.5% w/w or less, about 3% w/w or less, about 2.5% w/w or less, about 2% w/w or less, about 1.5% w/w or less, about 1% w/w or less, about 0.9% w/w or less, about 0.8% w/w or less, about 0.7% w/w or less, about 0.6% w/w or less, about 0.5% w/w or less, about 0.4% w/w or less, about 0.3% w/w or less, about 0.2% w/w or less, about 0.1% w/w or less, about 0.09% w/w or less, about 0.08% w/w or less, about 0.07% w/w or less, about 0.06% w/w or less, about 0.05% w/w or less, about 0.04% w/w or less, about 0.03% w/w or less, about 0.02% w/w or less, or about 0.01% w/w or less total impurities (e.g., Impurity F, Impurity J, Impurity A, Impurity B, Impurity C, etc.) upon storage at about 40° C. and about 75% RH for an extended period (e.g., at least two weeks, at least three weeks, at least four weeks, at least six weeks, at least two months, at least four months, at least six months, at least twelve months, at least eighteen months, or at least two years).

In some embodiments, the formulation comprises about 20% w/w or less, about 15% w/w or less, about 10% w/w or less, about 9% w/w or less, about 8% w/w or less, about 7% w/w or less, about 6% w/w or less, about 5% w/w or less, about 4.5% w/w or less, about 4% w/w or less, about 3.5% w/w or less, about 3% w/w or less, about 2.5% w/w or less, about 2% w/w or less, about 1.5% w/w or less, about 1% w/w or less, about 0.9% w/w or less, about 0.8% w/w or less, about 0.7% w/w or less, about 0.6% w/w or less, about 0.5% w/w or less, about 0.4% w/w or less, about 0.3% w/w or less, about 0.2% w/w or less, about 0.1% w/w or less, about 0.09% w/w or less, about 0.08% w/w or less, about 0.07% w/w or less, about 0.06% w/w or less, about 0.05% w/w or less, about 0.04% w/w or less, about 0.03% w/w or less, about 0.02% w/w or less, or about 0.01% w/w or less total impurities (e.g., Impurity F, Impurity J, Impurity A, Impurity B, Impurity C, etc.) upon storage at about 40° C. and about 75% RH for about 1 month, about 2 months, about 3, months, about 4 months, about 5 months, about 6 months, about 7 months, about 8 months, about 9 months, about 10 months, about 11 months, about 12 months, about 14 months, about 16 months, about 18 months, about 20 months, about 22 months, about 24 months, about 26 months, about 28 months, about 30 months, about 32 months, about 34 months, about 36 months, about 38 months, about 40 months, about 42 months, about 44 months, about 46 months, or about 48 months.

Properties of the Formulations

In some embodiments, the formulation has an osmolality of from about 100 mOsm/kg to about 500 mOsm/kg. In some embodiments, the formulation has an osmolality of from about 150 mOsm/kg to about 450 mOsm/kg. In some embodiments, the formulation has an osmolality of from about 175 mOsm/kg to about 400 mOsm/kg. In some embodiments, the formulation has an osmolality of from about 200 mOsm/kg to about 375 mOsm/kg. In some embodiments, the formulation has an osmolality of from about 225 mOsm/kg to about 350 mOsm/kg. In some embodiments, the formulation has an osmolality of from about 250 mOsm/kg to about 350 mOsm/kg. In some embodiments, the formulation has an osmolality of from about 270 mOsm/kg to about 330 mOsm/kg.

In some embodiments, the formulation has an osmolality of at least about 150 mOsm/kg. In some embodiments, the formulation has an osmolality of at least about 175 mOsm/kg. In some embodiments, the formulation has an osmolality of at least about 200 mOsm/kg. In some embodiments, the formulation has an osmolality of at least about 225 mOsm/kg. In some embodiments, the formulation has an osmolality of at least about 250 mOsm/kg. In some embodiments, the formulation has an osmolality of at least about 275 mOsm/kg. In some embodiments, the formulation has an osmolality of at least about 300 mOsm/kg. In some embodiments, the formulation has an osmolality of at least about 325 mOsm/kg. In some embodiments, the formulation has an osmolality of at least about 350 mOsm/kg. In some embodiments, the formulation has an osmolality of at least about 375 mOsm/kg. In some embodiments, the formulation has an osmolality of at least about 400 mOsm/kg.

In some embodiments, the formulation is isotonic to a human plasma.

In some embodiments, the formulation has an osmolality of about 300 mOsm/kg.

In some embodiments, the osmolality of the formulation is measured at about 1 day, about 2 days, about 3 days, about 4 days, about 5 days, about 6 days, about 7 days, about 14 days, about 20 days, about 1 month, about 2 months, about 3, months, about 4 months, about 5 months, about 6 months, about 7 months, about 8 months, about 9 months, about 10 months, about 11 months, about 12 months, about 14 months, about 16 months, about 18 months, about 20 months, about 22 months, about 24 months, about 26 months, about 28 months, about 30 months, about 32 months, about 34 months, about 36 months, about 38 months, about 40 months, about 42 months, about 44 months, about 46 months, or about 48 months after storage of the formulation as described herein.

In some embodiments, the formulation has a pH value ranging from about 3.5 to about 7.0, from about 3.6 to about 6.9, from about 3.7 to about 6.8, from about 3.8 to about 6.7, from about 3.9 to about 6.6, from about 4.0 to about 6.5, from about 4.1 to about 6.4, from about 4.2 to about 6.3, from about 4.3 to about 6.2, from about 4.4 to about 6.1, from about 4.5 to about 6.0, from about 4.5 to about 5.9, from about 4.5 to about 5.8, from about 4.5 to about 5.7, from about 4.5 to about 5.6, or from about 4.5 to about 5.5.

In some embodiments, the formulation has a pH value of about 4.0, about 4.1, about 4.2, about 4.3, about 4.4, about 4.5, about 4.6, about 4.7, about 4.8, about 4.9, about 5.0, about 5.1, about 5.2, about 5.3, about 5.4, about 5.5, about 5.6, about 5.7, about 5.8, about 5.9, about 6.0, about 6.1, about 6.2, about 6.3, about 6.4, about 6.6, about 6.7, about 6.8, about 6.9, or about 7.0.

In some embodiments, the formulation has a pH value of about 5.0±2.0, about 5.0±1.9, about 5.0±1.8, about 5.0±1.7, about 5.0±1.6, about 5.0±1.5, about 5.0±1.4, about 5.0±1.3, about 5.0±1.2, about 5.0±1.1, about 5.0±1.0, about 5.0±0.9, about 5.0±0.8, about 5.0±0.7, about 5.0±0.6, about 5.0±0.5, about 5.0±0.4, about 5.0±0.3, about 5.0±0.2, or about 5.0±0.1.

In some embodiments, the pH value of the formulation is measured at about 1 day, about 2 days, about 3 days, about 4 days, about 5 days, about 6 days, about 7 days, about 14 days, about 20 days, about 1 month, about 2 months, about 3, months, about 4 months, about 5 months, about 6 months, about 7 months, about 8 months, about 9 months, about 10 months, about 11 months, about 12 months, about 14 months, about 16 months, about 18 months, about 20 months, about 22 months, about 24 months, about 26 months, about 28 months, about 30 months, about 32 months, about 34 months, about 36 months, about 38 months, about 40 months, about 42 months, about 44 months, about 46 months, or about 48 months after storage of the formulation as described herein.

Stability

In some embodiments, the formulation remains stable for more than about four weeks, about five weeks, about six weeks, about seven weeks, about eight weeks, about nine weeks, about ten weeks, about eleven weeks, about twelve weeks, about thirteen weeks, about fourteen weeks, or about fifteen weeks after storage of the formulation as described herein.

In some embodiments, the formulation remains stable for more than about 1 month, about 2 months, about 3 months, about 4 months, about 5 months, about 6 months, about 7 months, about 8 months, about 9 months, about 10 months, about 11 months, about 12 months, about 13 months, about 14 months, about 15 months, about 16 months, about 17 months, about 18 months, about 19 months, about 20 months, about 21 months, about 22 months, about 24 months, about 26 months, about 28 months, about 30 months, about 32 months, about 34 months, about 36 months, about 38 months, about 40 months, about 42 months, about 44 months, about 46 months, or about 48 months after storage of the formulation as described herein.

In some embodiments, the formulation is stable after storage for at least one month, at least three months, at least six months, at least nine months, or at least twelve months under 25° C. and 60% RH.

In some embodiments, the formulation is stable after storage for at least one month, at least three months, at least six months, at least nine months, or at least twelve months under 40° C. and 75% RH.

In some embodiments, the concentration of Compound A or a pharmaceutically acceptable salt thereof in the formulation is stable, i.e., does not change or changes not more than about 25%, about 20%, about 19%, about 18%, about 17%, about 16%, about 15%, about 14%, about 13%, about 12%, about 11%, about 10%, about 9%, about 8%, about 7%, about 6%, about 5%, about 4%, about 3%, about 2%, about 1%, about 0.9%, about 0.8%, about 0.7%, about 0.6%, about 0.5%, about 0.4%, about 0.3%, about 0.2%, or about 0.1%, for more than about four weeks, about five weeks, about six weeks, about seven weeks, about eight weeks, about nine weeks, about ten weeks, about eleven weeks, about twelve weeks, about thirteen weeks, about fourteen weeks, or about fifteen weeks after storage of the formulation as described herein.

In some embodiments, the concentration of Compound A or a pharmaceutically acceptable salt in the formulation is stable, i.e., does not change or changes not more than about 25%, about 20%, about 19%, about 18%, about 17%, about 16%, about 15%, about 14%, about 13%, about 12%, about 11%, about 10%, about 9%, about 8%, about 7%, about 6%, about 5%, about 4%, about 3%, about 2%, about 1%, about 0.9%, about 0.8%, about 0.7%, about 0.6%, about 0.5%, about 0.4%, about 0.3%, about 0.2%, or about 0.1%, for more than about 1 month, about 2 months, about 3 months, about 4 months, about 5 months, about 6 months, about 7 months, about 8 months, about 9 months, about 10 months, about 11 months, about 12 months, about 13 months, about 14 months, about 15 months, about 16 months, about 17 months, about 18 months, about 19 months, about 20 months, about 21 months, about 22 months, about 23 months, about 24 months, about 26 month, about 28 month, about 30 month, about 32 month, about 34 month, about 36 month, about 38 month, about 40 month, about 42 month, about 44 month, about 46 month, or about 48 month after storage of the formulation as described herein.

In some embodiments, the amount of the impurities (e.g., Impurity F, Impurity J, Impurity A, Impurity B, Impurity C, etc.) in the formulation does not change or changes not more than about 25%, about 20%, about 19%, about 18%, about 17%, about 16%, about 15%, about 14%, about 13%, about 12%, about 11%, about 10%, about 9%, about 8%, about 7%, about 6%, about 5%, about 4%, about 3%, about 2%, about 1%, about 0.9%, about 0.8%, about 0.7%, about 0.6%, about 0.5%, about 0.4%, about 0.3%, about 0.2%, or about 0.1%, for more than about four weeks, about five weeks, about six weeks, about seven weeks, about eight weeks, about nine weeks, about ten weeks, about eleven weeks, about twelve weeks, about thirteen weeks, about fourteen weeks, or about fifteen weeks after storage of the formulation as described herein.

In some embodiments, the amount of impurities (e.g., Impurity F, Impurity J, Impurity A, Impurity B, Impurity C, etc.) in the formulation does not change or changes not more than about 25%, about 20%, about 19%, about 18%, about 17%, about 16%, about 15%, about 14%, about 13%, about 12%, about 11%, about 10%, about 9%, about 8%, about 7%, about 6%, about 5%, about 4%, about 3%, about 2%, about 1%, about 0.9%, about 0.8%, about 0.7%, about 0.6%, about 0.5%, about 0.4%, about 0.3%, about 0.2%, or about 0.1%, for more than about 1 month, about 2 months, about 3 months, about 4 months, about 5 months, about 6 months, about 7 months, about 8 months, about 9 months, about 10 months, about 11 months, about 12 months, about 13 months, about 14 months, about 15 months, about 16 months, about 17 months, about 18 months, about 19 months, about 20 months, about 21 months, about 22 months, about 24 months, about 26 months, about 28 months, about 30 months, about 32 months, about 34 months, about 36 months, about 38 months, about 40 months, about 42 months, about 44 months, about 46 months, or about 48 months after storage of the formulation as described herein.

In some embodiments, the osmolality in the formulation is stable, i.e., does not change or changes not more than about 25%, about 20%, about 19%, about 18%, about 17%, about 16%, about 15%, about 14%, about 13%, about 12%, about 11%, about 10%, about 9%, about 8%, about 7%, about 6%, about 5%, about 4%, about 3%, about 2%, about 1%, about 0.9%, about 0.8%, about 0.7%, about 0.6%, about 0.5%, about 0.4%, about 0.3%, about 0.2%, or about 0.1%, for more than about four weeks, about five weeks, about six weeks, about seven weeks, about eight weeks, about nine weeks, about ten weeks, about eleven weeks, about twelve weeks, about thirteen weeks, about fourteen weeks, or about fifteen weeks after storage of the formulation as described herein.

In some embodiments, the osmolality in the formulation is stable, i.e., does not change or changes not more than about 25%, about 20%, about 19%, about 18%, about 17%, about 16%, about 15%, about 14%, about 13%, about 12%, about 11%, about 10%, about 9%, about 8%, about 7%, about 6%, about 5%, about 4%, about 3%, about 2%, about 1%, about 0.9%, about 0.8%, about 0.7%, about 0.6%, about 0.5%, about 0.4%, about 0.3%, about 0.2%, or about 0.1%, for more than about 1 month, about 2 months, about 3 months, about 4 months, about 5 months, about 6 months, about 7 months, about 8 months, about 9 months, about 10 months, about 11 months, about 12 months, about 13 months, about 14 months, about 15 months, about 16 months, about 17 months, about 18 months, about 19 months, about 20 months, about 21 months, about 22 months, about 24 months, about 26 months, about 28 months, about 30 months, about 32 months, about 34 months, about 36 months, about 38 months, about 40 months, about 42 months, about 44 months, about 46 months, or about 48 months after storage of the formulation as described herein.

In some embodiments, the pH of the formulation is stable, i.e., does not change or changes within ±1.0, ±0.9, ±0.8, ±0.7, ±0.6, ±0.5, ±0.4, ±0.3, ±0.2, or ±0.1, for more than about four weeks, about five weeks, about six weeks, about seven weeks, about eight weeks, about nine weeks, about ten weeks, about eleven weeks, about twelve weeks, about thirteen weeks, about fourteen weeks, or about fifteen weeks after storage of the formulation as described herein.

In some embodiments, the pH of the formulation is stable i.e., does not change or changes within ±1.0, ±0.9, ±0.8, ±0.7, ±0.6, ±0.5, ±0.4, ±0.3, ±0.2, or ±0.1, for more than about 1 month, about 2 months, about 3 months, about 4 months, about 5 months, about 6 months, about 7 months, about 8 months, about 9 months, about 10 months, about 11 months, about 12 months, about 13 months, about 14 months, about 15 months, about 16 months, about 17 months, about 18 months, about 19 months, about 20 months, about 21 months, about 22 months, about 24 months, about 26 months, about 28 months, about 30 months, about 32 months, about 34 months, about 36 months, about 38 months, about 40 months, about 42 months, about 44 months, about 46 months, or about 48 months after storage of the formulation as described herein.

In some embodiments, the term "stable" means that the percentage, volume, or concentration of impurities (e.g., Impurity F, Impurity J, Impurity A, Impurity B, Impurity C, etc.), pH, Compound A or a pharmaceutically acceptable salt, osmolality, etc. does not change more than about 0.1%, about 0.2%, about 0.3%, about 0.4%, about 0.5%, about 0.6%, about 0.7%, about 0.8%, about 0.9%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, or about 25% from the original percentage, volume, or concentration, for example, after storage under a certain condition or being subjected to a certain treatment (e.g., heat, light exposure, humidity exposure).

Methods of Use

In some aspects, the present disclosure provides a method of treating or preventing a disease, comprising administering to a subject in need thereof a formulation disclosed herein.

In some aspects, the present disclosure provides a formulation disclosed herein for use in treating or preventing a disease in a subject in need thereof.

In some aspects, the present disclosure provides a method of alleviating a symptom of a disease in a subject in need thereof, comprising administering to the subject a formulation disclosed herein.

In some aspects, the present disclosure provides a formulation disclosed herein for use in alleviating a symptom of a disease in a subject in need thereof.

In some embodiments, the subject is an animal.

In some embodiments, the subject is a mammal.

In some embodiments, the subject in need thereof is a human.

In some embodiments, the pharmaceutical formulation in accordance with the present disclosure may be used for treatment of any of a variety of diseases, disorders, conditions, and/or symptoms including but not limited to one or more of the following: asthma, chronic obstructive pulmonary disease (COPD); bronchitis; emphysema; bronchiectasis; cystic fibrosis; sarcoidosis; alpha-1 antitrypsin deficiency; farmer's lung and related diseases; hypersensitivity pneumonitis; lung fibrosis; complications of lung transplantation; vasculitic disorders and thrombotic disorders of the lung vasculature, and pulmonary hypertension; cough; thrombotic or hemorrhagic stroke; acute and chronic rhinitis; perennial and seasonal allergic rhinitis; nasal polyposis; acute viral infection including the common cold, and infection due to respiratory syncytial virus, influenza, coronavirus (including SARS and SARS-CoV-2) and adenovirus; acute lung injury; acute respiratory distress syndrome (ARDS); pneumonia, including COVID-19 pneumonia; as well as exacerbations of each of the foregoing respiratory tract disease states, in particular exacerbations of ARDS and all types of pneumonia.

In some embodiments, the pharmaceutical formulation in accordance with the present disclosure may be used for treatment of acute respiratory distress syndrome (ARDS).

In some embodiments, the pharmaceutical formulation in accordance with the present disclosure may be used for alleviating a symptom associated with pneumonia, including COVID-19 pneumonia.

In some embodiments, the symptom associated with pneumonia, including COVID-19 pneumonia, is acute respiratory distress syndrome (ARDS).

In some embodiments, the formulation is pharmaceutically administered to the subject.

In some embodiments, the formulation is pharmaceutically administered to the subject using conventional modes of delivery including, but not limited to, intravenous, intraperitoneal, intraarterial, intrapleural, intrathecal, intramuscular, and subcutaneous administration.

In some embodiments, the formulation is pharmaceutically administered to the subject using intravenous administration (e.g., intravenous infusion or intravenous injection).

In some embodiments, the formulation is pharmaceutically administered to the subject using intravenous infusion.

In some embodiments, the therapeutically effective amount of the formulation is between about 50 mg and about 700 mg per day, between about 75 mg and about 600 mg per day, or between about 100 mg and about 500 mg per day.

In some embodiments, the therapeutically effective amount of the formulation is about 100 mg per day, about 150 mg per day, about 200 mg per day, about 250 mg per day, about 300 mg per day, about 350 mg per day, about 400 mg per day, about 450 mg per day, or about 500 mg per day.

Definitions

It is to be understood, as used herein, the term "Compound A" refers interchangeably to the compound identified by the IUPAC name of 4-[(4-methylpiperazin-1-yl)methyl]-N-[4-methyl-3-[(4-pyridin-3-ylpyrimidin-2-yl)amino]phenyl]benzamide, or a mesylate salt thereof, or any other pharmaceutically acceptable salt thereof.

It is understood that a crystal polymorphism may be present for the compounds represented by the formula. It is noted that any crystal form, crystal form mixture, or anhydrate or hydrate thereof is included in the scope of the present disclosure.

As used herein, the term "crystal polymorphs", "polymorphs" or "crystal forms" means crystal structures in which a compound (or a salt or solvate thereof) can crystallize in different crystal packing arrangements, all of which have the same elemental composition. Different crystal forms usually have different X-ray diffraction patterns, infrared spectral, melting points, density hardness, crystal shape, optical and electrical properties, stability and solubility. Recrystallization solvent, rate of crystallization, storage temperature, and other factors may cause one crystal form to dominate. Crystal polymorphs of the compounds can be prepared by crystallization under different conditions.

It is to be understood that all references to pharmaceutically acceptable salts include solvent addition forms (solvates) or crystal forms (polymorphs) as defined herein, of the same salt.

It is to be understood that the compounds of any formula described herein include the compounds themselves, as well as their salts, and their solvates, if applicable. A salt, for example, can be formed between an anion and a positively charged group (e.g., amino) on a substituted benzene compound. Suitable anions include chloride, bromide, iodide, sulfate, bisulfate, sulfamate, nitrate, phosphate, citrate, methanesulfonate, trifluoroacetate, glutamate, glucuronate, glutarate, malate, maleate, succinate, fumarate, tartrate, tosylate, salicylate, lactate, naphthalenesulfonate, and acetate (e.g., trifluoroacetate).

It is to be understood that the compounds of the present disclosure, for example, the salts of the compounds, can exist in either hydrated or unhydrated (the anhydrous) form or as solvates with other solvent molecules. Nonlimiting examples of hydrates include monohydrates, dihydrates, etc. Nonlimiting examples of solvates include ethanol solvates, acetone solvates, etc.

As used herein, the term "solvate" means solvent addition forms that contain either stoichiometric or non-stoichiometric amounts of solvent. Some compounds have a tendency to trap a fixed molar ratio of solvent molecules in the crystalline solid state, thus forming a solvate. If the solvent is water, the solvate formed is a hydrate; and if the solvent is alcohol, the solvate formed is an alcoholate. Hydrates are formed by the combination of one or more molecules of water with one molecule of the substance in which the water retains its molecular state as $H_2O$.

It is to be understood that the present disclosure provides methods for the preparation of the formulations described herein. The present disclosure also provides detailed methods for preparation of various formulations of the present disclosure according to the following Examples.

It is to be understood that, unless otherwise stated, any description of a method of treatment includes use of the compounds to provide such treatment as is described herein, as well as use of the compounds to prepare a medicament to treat such condition. The treatment includes treatment of human or non-human animals including rodents and other disease models.

It is to be understood that, unless otherwise stated, any description of a method of prevention includes use of the compounds to provide such prevention as is described herein, as well as use of the compounds to prepare a medicament to prevent such condition. The prevention includes prevention in human or non-human animals including rodents and other disease models.

As used herein, the term "subject" is interchangeable with the term "subject in need thereof", both of which refer to a subject having a disease or having an increased risk of developing the disease. A "subject" includes a mammal. The mammal can be e.g., a human or appropriate non-human mammal, such as primate, mouse, rat, dog, cat, cow, horse, goat, camel, sheep or pig. The subject can also be a bird or fowl. In one embodiment, the mammal is a human.

As used herein, the term "treating" or "treat" describes the management and care of a patient for the purpose of combating a disease, condition, or disorder and includes the administration of a compound of the present disclosure, or a pharmaceutically acceptable salt, polymorph or solvate thereof, to alleviate the symptoms or complications of a disease, condition or disorder, or to eliminate the disease, condition or disorder. The term "treat" can also include treatment of a cell in vitro or an animal model.

It is to be understood that a compound of the present disclosure, or a pharmaceutically acceptable salt, polymorph or solvate thereof, can or may also be used to prevent a relevant disease, condition or disorder, or used to identify suitable candidates for such purposes.

As used herein, the term "preventing," "prevent," or "protecting against" describes reducing or eliminating the onset of the symptoms or complications of such disease, condition or disorder.

As used herein, the term "pharmaceutically acceptable" refers to those compounds, anions, cations, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the term "pharmaceutically acceptable excipient" means an excipient that is useful in preparing a formulation that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient.

The formulations containing active compounds of the present disclosure may be manufactured in a manner that is generally known, e.g., by means of conventional mixing, dissolving, granulating, levigating, emulsifying, entrapping, or lyophilizing processes. Pharmaceutical compositions may be formulated in a conventional manner using one or more pharmaceutically acceptable carriers comprising excipients and/or auxiliaries that facilitate processing of the active compounds into preparations that can be used pharmaceutically.

It is to be understood that the pharmaceutical compositions can be included in a container, pack, or dispenser together with instructions for administration.

As used herein, the term "pharmaceutically acceptable salts" refer to derivatives of the compounds of the present disclosure wherein the parent compound is modified by making acid or base salts thereof. In some embodiments, the pharmaceutically acceptable salt of a compound (e.g., a β-lactam compound or probenecid described herein) is also a prodrug of the compound. Examples of pharmaceutically acceptable salts include, but are not limited to, mineral or organic acid salts of basic residues such as amines, alkali or organic salts of acidic residues such as carboxylic acids, and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 2-acetoxybenzoic, 2-hydroxyethane sulfonic, acetic, ascorbic, benzene sulfonic, benzoic, bicarbonic, carbonic, citric, edetic, ethane disulfonic, 1,2-ethane sulfonic, fumaric, glucoheptonic, gluconic, glutamic, glycolic, glycollyarsanilic, hexylresorcinic, hydrabamic, hydrobromic, hydrochloric, hydroiodic, hydroxymaleic, hydroxynaphthoic, isethionic, lactic, lactobionic, lauryl sulfonic, maleic, malic, mandelic, methane sulfonic, napsylic, nitric, oxalic, pamoic, pantothenic, phenylacetic, phosphoric, polygalacturonic, propionic, salicylic, stearic, subacetic, succinic, sulfamic, sulfanilic, sulfuric, tannic, tartaric, toluene sulfonic, and the commonly occurring amine acids, e.g., glycine, alanine, phenylalanine, arginine, etc.

Other examples of pharmaceutically acceptable salts include hexanoic acid, cyclopentane propionic acid, pyruvic acid, malonic acid, 3-(4-hydroxybenzoyl)benzoic acid, cinnamic acid, 4-chlorobenzenesulfonic acid, 2-naphthalenesulfonic acid, 4-toluenesulfonic acid, camphorsulfonic acid, 4-methylbicyclo-[2.2.2]-oct-2-ene-1-carboxylic acid, 3-phenylpropionic acid, trimethylacetic acid, tertiary butylacetic acid, muconic acid, and the like. The present disclosure also encompasses salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like. In the salt form, it is understood that the ratio of the compound to the cation or anion of the salt can be 1:1, or any ration other than 1:1, e.g., 3:1, 2:1, 1:2, or 1:3.

It is to be understood that all references to pharmaceutically acceptable salts include solvent addition forms (solvates) or crystal forms (polymorphs) as defined herein, of the same salt.

The dosage regimen utilizing the compounds is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition.

All percentages and ratios used herein, unless otherwise indicated, are by weight. Other features and advantages of the present disclosure are apparent from the different examples. The provided examples illustrate different components and methodology useful in practicing the present disclosure. The examples do not limit the claimed disclosure. Based on the present disclosure the skilled artisan can identify and employ other components and methodology useful for practicing the present disclosure.

All publications and patent documents cited herein are incorporated herein by reference as if each such publication or document was specifically and individually indicated to be incorporated herein by reference. Citation of publications and patent documents is not intended as an admission that any is pertinent prior art, nor does it constitute any admission as to the contents or date of the same. The invention having now been described by way of written description, those of skill in the art will recognize that the invention can be practiced in a variety of embodiments and that the foregoing description and examples below are for purposes of illustration and not limitation of the claims that follow.

EXAMPLES

| List of Abbreviations | |
| --- | --- |
| ABL | Abelson-related gene |
| ARDS | Acute Respiratory Distress Syndrome |
| CAPB | 4-[(4-methyl-1-piperazinyl)methyl]benzoic acid dihydrochloride |
| CFU | Colony Forming Unit |
| CML | chronic myelogenous leukemia |
| DDR-1 | Discoidin domain receptor family, member 1 |
| GC | gas chromatography |
| HPLC | high performance liquid chromatography |
| iv | intravenous |
| KIT | Proto-oncogene receptor tyrosine kinase |
| LC | high pressure liquid chromatography |
| LOD | limit of detection |
| LOQ | limit of quantitation |
| NLT | not less than |

| List of Abbreviations | |
| --- | --- |
| NMT | not more than |
| PDGFR | Platelet-derived growth factor receptor |
| Ph Eur | European Pharmacopoeia |
| ppm | parts per million |
| R2 | Coefficient of Determination |
| RH | Relative humidity |
| RRT | Relative retention time |
| RSD | Relative Standard Deviation |
| USP | United States Pharmacopeia |
| UV | Ultraviolet |
| v/v | volume/volume |
| WFI | Water for Injection |
| w/w | weight/weight |

Example 1. Formulation Development

Imatinib mesylate is soluble in aqueous solution. Previous studies showed good solubility and stability at 50 mg/ml. Development of an 8 mg/ml solution was appropriate for the acceptable clinical use requirements. Four 8 mg/ml solution formulations were screened for acceptable solubility and accelerated stability investigations:

Formulation 1—Water only (pH 5.3—no adjustment). Osmolality 15 mOsmol/kg

Formulation 2—5% w/w Dextrose (pH 5.0—no adjustment). Osmolality 309 mOsmol/kg

Formulation 3—0.05 M acetate buffer (pH 5.0). Osmolality 95 mOsmol/kg

Formulation 4—0.01 M acetate buffer (pH 5.0), 1.9% v/v Glycerol. Osmolality 304 mOsmol/kg After 21 days storage (solutions were in sealed glass vials) at 40° C. and 60° C., all formulations exhibited no degradation (initial and all timepoints were <0.05%) and no precipitation.

Formulation 4 is further exemplified. The formulation was a buffered, isotonic sterile solution for infusion of imatinib 8 mg/ml, equivalent to 9.557 mg/ml of imatinib mesylate. The buffer used was 0.01 M acetate buffer (adjusted to pH 5.0) and the tonicity adjustment was by use of glycerol. The formulation was presented as 40 ml fill volume within a 50 ml clear glass vial with chlorobutyl stopper and aluminum flip-off seal. Alternatively, the formulation was made as 25 ml fill volume. The composition of the formulation is shown in Tables 1-1 and 1-2.

TABLE 1-1

Composition of Imatinib mesylate 8 mg/ml solution (40 ml fill)

| Component | Function | Amount per vial |
| --- | --- | --- |
| Imatinib mesylate | Active substance | 382.28 mg * |
| Glycerol anhydrous | Tonicity adjuster | 960.0 mg (0.76ml) |
| Sodium acetate, anhydrous | Buffer | 22.1 mg |
| Acetic acid (glacial) 100% | Buffer | 7.84 mg |
| Sodium hydroxide | pH adjustment | QUANTITY SUFFICIENT |
| Hydrochloric acid | pH adjustment | QUANTITY SUFFICIENT |
| Water for Injection | Vehicle | to 40.0 ml |

* equal to 8.0 mg of imatinib base per ml.

TABLE 1-2

| Composition of Imatinib mesylate 8 mg/ml solution (25 ml fill) | | |
|---|---|---|
| Component | Function | Amount per vial |
| Imatinib mesylate | Active substance | 238.93 mg * |
| Glycerol anhydrous | Tonicity adjuster | 600.0 mg |
| Sodium acetate, trihydrate | Buffer | 22.75 mg |
| Acetic acid (glacial) 100% | Buffer | 4.90 mg |
| Sodium hydroxide | pH adjustment | QUANTITY SUFFICIENT |
| Hydrochloric acid | pH adjustment | QUANTITY SUFFICIENT |
| Water for Injection | Vehicle | to 25.0 ml |

* equal to 8.0 mg of imatinib base per ml.

Example 2. Preparation/Manufacture of Formulations

Various batch formulation preparations are shown in Tables 2-1 and 2-2.

TABLE 2-1

| Batch formulation | | |
|---|---|---|
| Component | Amount | % |
| Imatinib mesylate | 1160.00 g (note 1) | 0.8% (w/v) |
| Glycerol anhydrous | 3474.06 g | 2.39% (w/v) |
| | | 1.9% (v/v) |
| Sodium acetate, Anhydrous | 79.75 g | 0.055% (w/v) |
| Acetic acid (glacial) 100% | 28.42 g | 0.0196% (w/v) |
| Sodium hydroxide | note 2 | |
| Hydrochloric acid | note 2 | |
| Water for Injection | QUANTITY SUFFICIENT 146,160 g (note 3) | to 100.00 % (w/v) |
| Total | 146,160 g (145.0 liters) | 100% (w/v) | note 1
correction for mesylate salt, assay as anhydrous base and % water content applied in batch manufacturing
note 2
1N solutions of HCL and NaOH prepared during manufacture and used as required for pH adjustment to 5.0
note 3
density = 1.008 g/ml

TABLE 2-2

| Batch formulation | | |
|---|---|---|
| Component | Amount | % |
| Imatinib mesylate | 1815.83 g (note 1) | 0.8% (w/v) |
| Glycerol anhydrous | 4560.0 g | 2.39% (w/v) |
| | | 1.9% (v/v) |
| Sodium acetate, trihydrate | 172.9 g | 0.091% (w/v) |
| Acetic acid (glacial) 100% | 37.24 g | 0.0196% (w/v) |
| Sodium hydroxide | note 2 | |
| Hydrochloric acid | note 2 | |
| Water for Injection | QUANTITY SUFFICIENT 191,520 g (note 3) | to 100.00% (w/v) |
| Total | 191,520 g (190.0 liters) | 100% (w/v) | note 1
correction for mesylate salt, assay as anhydrous base and % water content applied in batch manufacturing
note 2
1N solutions of HCL and NaOH prepared during manufacture and used as required for pH adjustment to 5.0
note 3
density = 1.008 g/ml Manufacture of the Bulk Solution The manufacturing process for the batch formulation generally begins with preparing a bulk solution under sterile condition, for example, in a Class C (10000 or better) area. Various excipients are added to form a solution, and pH adjusted as needed. Imatinib mesylate is then added, and the solution pH is checked and adjusted as needed. Water for Injection is then used to make up to the final volume. In-process samples are taken for pre-filtration bioburden, density, pH and assay.

Sterile Filtration of the Bulk Solution, Vial Filling and Sealing

All operations are performed under sterile condition, for example, within a Grade A (Class 100) Laminar Flow Hood contained within a Grade B (Class 1000) sterile area. Sterilization can be achieved by filtration, for example, by passing a bulk solution through two in-series 0.22 μm filters. Sterile-filtered solution is then filled into vials, such as through tubing from the post-filtration side aseptically connected to the vial filling and sealing equipment. Samples for sterility and endotoxin testing can be taken during this process and a filter integrity test can be performed at the end of the sterile filtration process. Visual inspection can be performed on all the vials and finally samples can be taken for release testing.

Example 3. Engineering Batch—Stability Study Results

The engineering batch was placed on stability study. This batch was manufactured according to the process described in Example 2 and was therefore representative of the batch for the clinical study.

The stability of engineering batch samples was tested. Samples were then stored at 25° C./60% relative humidity (RH) and were tested after 1 month, 3 month, 6 month and 9 month. The results of the tests are shown in Table 3-1 below. Samples were also stored at 40° C./75% RH and were tested after 1 month, 3 month and 6 month. The results of the tests are shown in Table 3-2 below.

The 6-month stability data (at both 25° C./60% RH and 40° C./75% RH) show no change from the initial data. These data support the assignment of at least 18 month shelf-life at 25° C.

TABLE 3

| Engineering Batch - Stability Study Results | |
|---|---|
| Strength: | Imatinib 8 mg/mL |
| Batch Size: | 17 liters (~350 vials) |

TABLE 3-1

Stability Data from storage at 25° C./60% RH (stored inverted)

| Test | Specification | Initial | 1 month | 3 months | 6 months | 9 months |
|---|---|---|---|---|---|---|
| Appearance | Clear, yellow solution, free from visible particles | Complies | Complies | Complies | Complies | Complies |
| Identification (LC-UV) | The retention time of the principal peak in the chromatogram of the sample solution corresponds to that in the chromatogram of the standard solution | Complies | Complies | Complies | Complies | Complies |
| Assay | 7.2-8.8 mg/mL | 8.0 mg/ml | 8.0 mg/ml | 8.0 mg/ml | 8.0 mg/ml | 8.0 mg/ml |
| Impurities and Degradation Products | Reporting Threshold: 0.05% (w/w) Unspecified and Unidentified Impurities: ≤0.1% (w/w) Specified Impurities: | All peaks ≥0.05% w/w reported RRT 1.11-0.05% (w/w) | All peaks ≥0.05% w/w reported <0.05% (w/w) | All peaks ≥0.05% w/w reported <0.05% (w/w) | All peaks ≥0.05% w/w reported RRT 0.79-0.01% <0.05% (w/w) | All peaks ≥0.05% w/w reported <0.05% (w/w) |
| | Impurity A: NMT 0.03% (w/w) | <LOQ | <LOQ | <LOQ | <LOQ | <LOQ |
| | Iniatinib EP Impurity F: NMT 0.03% (w/w) | <LOQ | <LOQ | <LOQ | <LOQ | <LOQ |
| | Imatinib EP Impurity J: NMT 0.2% (w/w) | <LOQ | <LOQ | <LOQ | <LOQ | <LOQ |
| | RRT 0.66: NMT 0.2% (w/w) | <LOQ | <LOQ | <LOQ | <LOQ | <LOQ |
| | RRT 0.71: NMT 0.2% (w/w) | <LOQ | <LOQ | <LOQ | <LOQ | <LOQ |
| | Total Impurities: ≤2.0% (w/w) | 0.05% (w/w) | 0.05% (w/w) | 0.05% (w/w) | 0.01% (w/w) | 0.05% (w/w) |
| pH | 4.5-5.5 | 5.1 | 5.1 | 5.1 | 5.1 | 5.0 |
| Osmolality | 270-330 mOsmol/kg | 309 mOsmol/kg | 310 mOsmol/kg | 311 mOsmol/kg | 311 mOsmol/kg | 309 mOsmol/kg |
| Particulate Contamination (see Note 1) | ≥10 μm: NMT 6000 particles/vial ≥25 μm: NMT 600 particles/vial | ≥10 μm: 37 particles/vial ≥25 μm: 0 particles/vial | Not tested | Not tested | Not tested | Not tested |
| Extractable Volume (see Note 2) | NLT 40 ml | 40 ml | Not tested | Not tested | Not tested | Not tested |

Note 1
These tests were performed only at the initial, 12 m, 24 m. and 36 m stability timepoints
Note 2
Only performed on the initial

TABLE 3-2

Stability Data from storage at 40° C./75% RH (stored inverted)

| Test | Specification | Initial | 1 month | 3 months | 6 months |
|---|---|---|---|---|---|
| Appearance | Clear, yellow solution, free from visible particles | Complies | Complies | Complies | Complies |
| Identification (LC-UV) | The retention time of the principal peak in the chromatogram of the sample solution corresponds to that in the chromatogram of the standard solution | Complies | Complies | Complies | Complies |
| Assay | 7.2-8.8 mg/mL | 8.0 mg/ml | 8.0 mg/ml | 8.0 mg/ml | 8.0 mg/ml |
| Impurities and Degradation Products | Reporting Threshold: 0.05% (w/w) Unspecified and Unidentified Impurities: ≤0.1% (w/w) Specified Impurities: | All peaks ≥0.05% w/w reported RRT 1.11-0.05% (w/w) | All peaks ≥0.05% w/w reported <0.05% (w/w) | All peaks ≥0.05% w/w reported < 0.05% (w/w) | All peaks ≥0.05% w/w reported <0.05% (w/w) |
| | Impurity A: NMT 0.03% (wAv) | <LOQ | <LOQ | <LOQ | <LOQ |
| | Iinatinib EP Impurity F: NMT 0.03% (w/w) | <LOQ | <LOQ | <LOQ | <LOQ |
| | Imatinib EP Impurity J: NMT 0.2% (w/w) | <LOQ | <LOQ | <LOQ | <LOQ |
| | RRT 0.66: NMT 0.2% (w/w) | <LOQ | <LOQ | <LOQ | <LOQ |
| | RRT 0.71: NMT 0.2% (w/w) | <LOQ | <LOQ | <LOQ | <LOQ |
| | Total Impurities: ≤2.0% (w/w) | 0.05% (w/w) | 0.05% (w/w) | 0.05% (w/w) | 0.10% (w/w) |
| pH | 4.5-5.5 | 5.1 | 5.1 | 5.1 | 5.0 |
| Osmolality | 270-330 mOsmol/kg | 309 mOsmol/kg | 309 mOsmol/kg | 311 mOsmol/kg | 310 mOsmol/kg |
| Particulate | ≥10 μm: NMT 6000 particles/vial | ≥10 μm: | Not tested | Not tested | Not tested |

TABLE 3-2-continued

Stability Data from storage at 40° C./75% RH (stored inverted)

| Test | Specification | Initial | 1 month | 3 months | 6 months |
|---|---|---|---|---|---|
| Contamination (see Note 1) | ≥25 μm: NMT 600 particles/vial | 37 particles/vial ≥25 μm: 0 particles/vial | | | |
| Extractable Volume (see Note 2) | NLT 40 ml | 40 ml | Not tested | Not tested | Not tested |

Note 1
These tests are performed only at the initial, 12 m, 24 m, and 36 m stability timepoints
Note 2
Only performed on the initial

Example 4. Clinical Batch—Stability Study Results

The clinical batch was placed on stability study. This batch was manufactured according to the process described in Example 2.

The stability of clinical batch samples was tested. Samples were then stored at 25° C./60% relative humidity (RH) and were tested after 1 month, 3 month and 6 month. The results of the tests are shown in Table 4-1 below. Samples were also stored at 40° C./75% RH and were tested after 1 month, 3 month and 6 month. The results of the tests are shown in Table 4-2 below.

The 6 month stability data (at both 25° C./60% RH and 40° C./75% RH) show no change whatsoever from the initial data. These data support the assignment of at least 18 month shelf-life at 25° C.

TABLE 4

Clinical Batch - Stability Study Results

| Batch Size: | 145 Liters (~3500 vials) |
|---|---|

Table 4-1

Stability Data from storage at 25° C./60% RH (stored inverted)

| Test | Specification | Initial | 1 month | 3 months | 6 months |
|---|---|---|---|---|---|
| Appearance | Clear, yellow solution, free from visible particles | Complies | Complies | Complies | Complies |
| Identification (LC-UV) | The retention time of the principal peak in the chromatogram of the sample solution corresponds to that in the chromatogram of the standard solution | Complies | Complies | Complies | Complies |
| Assay | 7.2-8.8 mg/mL | 8.1 mg/ml | 7.9 mg/ml | 7.9 mg/ml | 8.0 mg/ml |
| Impurities and Degradation Products (see Note 1) | Reporting Threshold: 0.05% (w/w) Unspecified and Unidentified Impurities: ≤0.1% (w/w) Specified Impurities: | All peaks ≥0.05% w/w reported <0.05% (w/w) | All peaks ≥0.05% w/w reported <0.05% (w/w) | All peaks ≥0.05% w/w reported <0.05% (w/w) | All peaks ≥0.05% w/w reported <0.05% (w/w) |
| | Impurity A: NMT 0.03% (w/w) | <LOD | <LOD | <LOD | <LOD |
| | Imatinib EP Impurity F: NMT 0.03% (w/w) | <LOD | <LOD | <LOD | <LOD |
| | Imatinib EP Impurity J: NMT 0.2% (w/w) | 0.013% (w/w) | <LOQ | 0.011% (w/w) | <LOQ |
| | RRT 0.66: NMT 0.2% (w/w) | <LOD | <LOD | <LOD | <LOD |
| | RRT 0.71: NMT 0.2% (w/w) | <LOD | <LOD | <LOD | <LOQ |
| | Total Impurities: ≤2.0% (w/w) | 0.06% (w/w) | 0.06% (w/w) | 0 08% (w/w) | 0.08% (w/w) |
| pH | 4.5-5.5 | 5.1 | 5.0 | 5.0 | 5.1 |
| Osmolality | 270-330 mOsmol/kg | 304 mOsmol/kg | 304 mOsmol/kg | 304 mOsmol/kg | 303 mOsmol/kg |
| Particulate Contamination (see Note 2) | ≥10 μm: NMT 6000 particles/vial ≥25 μm: NMT 600 particles/vial | ≥10 μm: 21 particles/vial ≥25 μm: 5 particles/vial | Not tested | Not tested | Not tested |
| Extractable Volume (see Note 3) | NLT 40 ml | 40 ml | Not tested | Not tested | Not tested |
| Container Closure Integrity (see Note 4) | Pass | Pass | Not tested | Not tested | Not tested |
| Bacterial Endotoxins (see Note 4) | NMT 3.5 IU/mg | LT 1.5 IU/mg | Not tested | Not tested | Not tested |

Table 4-1-continued

| | Stability Data from storage at 25° C./60% RH (stored inverted) | | | | |
|---|---|---|---|---|---|
| Test | Specification | Initial | 1 month | 3 months | 6 months |
| Sterility (see Note 5) | No growth | No growth | Not tested | Not tested | Not tested |

Note 1:
LOD is 0.003% w/w for Impurity A, RRT 0.66 and RRT 0.71.
LOD is 0.0015% w/w for Imatinib EP Impurity F
LOQ is 0.01% w/w for Imatinib EP Impurity J
LOQ is 0.01% w/w for Impurity A
Note 2:
Particulate Contamination performed at the initial. 12 m, 24 m and 36 m timepoints
Note 3:
Extractable Volume only performed at the initial timepoint
Note 4:
Container Closure Integrity and Bacterial Endotoxins performed at the initial, 12 m and 24 m timepoints
Note 5:
Sterility performed at the initial and 36m timepoints

TABLE 4-2

| | Stability Data from storage at 40° C./75% RH (stored inverted) | | | | |
|---|---|---|---|---|---|
| Test | Specification | Initial | 1 month | 3 months | 6 months |
| Appearance | Clear, yellow solution, free from visible particles | Complies | Complies | Complies | Complies |
| Identification (LC-UV) | The retention time of the principal peak in the chromatogram of the sample solution corresponds to that in the chromatogram of the standard solution | Complies | Complies | Complies | Complies |
| Assay | 7.2-8.8 mg/mL | 8.1 mg/ml | 7.9 mg/ml | 7.9 mg/ml | 8.0 mg/ml |
| Impurities and Degradation Products (see Note 1) | Reporting Threshold: 0.05% (w/w) | All peaks ≥0.05% w/w reported | All peaks ≥0.05% w/w reported | All peaks ≥0.05% w/w reported | All peaks ≥0.05% w/w reported |
| | Unspecified and Unidentified Impurities: ≤0.1% (w/w) | <0.05% (w/w) | RRT: 0.19 0.068% (w/w) | < 0.05% (w/w) | < 0.05% (w/w) |
| | Specified Impurities: | | | | |
| | Impurity A: NMT 0.03% (w/w) | <LOD | <LOD | <LOQ | <LOQ |
| | Imatinib EP Impurity F: NMT 0.03% (w/w) | <LOD | <LOD | <LOD | <LOD |
| | Imatinib EP Impurity J: NMT 0.2% (w/w) | 0 013% (w/w) | < LOQ | 0.012% (w/w) | 0.011% (w/w) |
| | RRT 0.66: NMT 0.2% (w/w) | <LOD | <LOD | <LOD | <LOD |
| | RRT 0.71: NMT 0.2% (w/w) | <LOD | <LOD | <LOD | <LOQ |
| | Total Impurities: ≤2.0% (w/w) | 0 06% (w/w) | 0.07% (w/w) | 0.08% (wAv) | 0.10% (w/w) |
| pH | 4.5-5.5 | 5.1 | 5.0 | 5.0 | 5.1 |
| Osmolality | 270-330 mOsmol/kg | 304 mOsmol/kg | 304 mOsmol/kg | 302 mOsmol/kg | 305 mOsmol/kg |
| Particulate Contamination (see Note 2) | ≥10 μm: NMT 6000 particles/vial ≥25 μm: NMT 600 particles/vial | ≥10 μm: 21 particles/vial ≥25 μm: 5 particles/vial | Not tested | Not tested | Not tested |
| Extraclabic Volume (see Note 3) | NLT 40ml | 40 ml | Not tested | Not tested | Not tested |
| Container Closure Integrity (see Note 4) | Pass | Pass | Not tested | Not tested | Not tested |
| Badcrial Endotoxins (see Note 4) | NMT 3.5 IU/mg | LT 1.5 IU/mg | Not tested | Not tested | Not tested |

TABLE 4-2-continued

| | Stability Data from storage at 40° C./75% RH (stored inverted) | | | | |
|---|---|---|---|---|---|
| Test | Specification | Initial | 1 month | 3 months | 6 months |
| Sterility (see Note 5) | No growth | No growth | Not tested | Not tested | Not tested |

Note 1:
LOD is 0.003% w/w for Impurity A, RRT 0.66 and RRT 0.71.
LOD is 0.0015% w/w for Imatinib EP Impurity F
LOQ is 0.01% w/w for Imatinib EP Impurity J
LOQ is 0.01% w/w for Impurity A
Note 2:
Particulate Contamination performed at the initial, 12 m, 24 m and 36 m timepoints
Note 3:
Extractable Volume only performed at the initial timepoint
Note 4:
Container Closure Integrity and Bacterial Endotoxins performed at the initial, 12 m and 24 m timepoints
Note 5:
Sterility performed at the initial and 36 m timepoints Example 5. Stability Study Results Additional stability studies were conducted under storage condition at 25° C./60% relative humidity (RH) or 40° C./75%. The results of the studies are shown in Tables 5-1-5-5 below.

TABLE 5-1

| | Stability Data from storage at 5° C. (stored inverted) | | | |
|---|---|---|---|---|
| Test | Specification | Initial | 1 month | 3 months |
| Appearance | Colorless to slightly greenish-yellow solution | Slightly greenish-yellow solution | Slightly greenish-yellow solution | Slightly greenish-yellow solution |
| | Solution free of visible particles | Particulates observed | Particulates observed | Particulates observed |
| | Clear solution | Clear solution | Clear solution | Clear solution |
| Assay | 7.6-8.4 mg/mL | 7.9 mg/ml | 8.0 mg/ml | 7.9 mg/ml |
| Impurities and Degradation Products | Unspecified and Unidentified Impurities: ≤0.1% (w/w) | RRT 0.76 <LOQ<br>RRT 0.80 <LOQ<br>Imatinib EP Impurity C: 0.03%<br>RRT 0.92 <LOQ<br>Imatinib Para-PPA Impurity: <LOQ<br>RRT 1.05: 0.01%<br>RRT 1.06: 0.02%<br>RRT 1.09 <LOD<br>RRT 1.107 <LOQ<br>RRT 1.114: 0.02%<br>RRT 1.14: 0.01%<br>RRT 1.147: 0.01%<br>RRT 1.155: 0.03%<br>RRT 1.167: 0.01%<br>RRT 1.174: 0.01% | RRT 0.76 <LOQ<br>RRT 0.80 <LOQ<br>Imatinib EP Impurity C: 0.01%<br>RRT 0.92 <LOQ<br>Imatinib Para-PPA Impurity: <LOQ<br>RRT 0.98 <LOD<br>RRT 0.99 <LOD<br>RRT 1.03: 0.02%<br>RRT 1.05: 0.01%<br>RRT 1.06: 0.02%<br>RRT 1.12: 0.01% | RRT 0.76 <LOQ<br>RRT 0.80 <LOQ<br>RRT 0.81 <LOD<br>RRT 0.87 <LOD<br>Imatinib EP Impurity C: 0.02%<br>RRT 0.92 <LOQ<br>Imatinib Para-PPA Impurity: <LOQ<br>RRT 1.03: 0.03%<br>RRT 1.04. 0.02%<br>RRT 1.06: 0.01%<br>RRT 1.12: 0.02% |
| | Specified Impurities: | | | |
| | Impurity A: NMT 0.03% (w/w) | ND | ND | ND |
| | Imatinib EP Impurity F: NMT 0.03% (w/w) | ND | ND | ND |
| | Imatinib EP Impurity J: NMT 0.2% (w/w) | 0.03% | 0.04% | 0.04% |
| | RRT 0.66: NMT 0.2% (w/w) | ND | ND | ND |
| | RRT 0.71: NMT 0.2% (w/w) | ND | ND | <LOD |
| | Total Impurities: ≤2.0% (w/w) | 0.19% | 0.11% | 0.13% |
| pH | 4.5-5.5 | 5.1 | 5.1 | 5.1 |
| Osmolality | 270-330 mOsmol/kg | 302 mOsmol/kg | 304 mOsmol/kg | 305 mOsmol/kg |
| Particulate Contamination | ≥10 µm: NMT 6000 particles/vial | ≥10 µm: 65 particles/vial | ≥10 µm: 20 particles/vial | ≥10 µm: 15 particles/vial |
| | ≥25 µm: NMT 600 particles/vial | ≥25 µm: 17 particles/vial | ≥25 µm 2 particles/vial | ≥25 µm: 0 particles/vial |

Note:
ND = Not Detected
LOD for Imatinib EP Impurity F is 0.0016% (w/w)
LOQ for Imatinib EP Impurity F is 0.005% (w/w)
LOD is 0.0033% w/w for all other Specified Impurities
LOQ is 0.010% w/w for all other Specified Impurities
For all Unspecified and Unidentified Impurities LOD is 0.0033% w/w and LOQ is 0.010% w/w

TABLE 5-2

Stability Data (laboratory batch) from storage at 25° C./60% RH (stored inverted)

| Test | Specification | Initial | 1 month | 3 months |
|---|---|---|---|---|
| Appearance | Colorless to slightly greenish-yellow solution<br>Solution free of visible particles<br>Clear solution | Slightly greenish-yellow solution<br>Particulates observed<br>Clear solution | Slightly greenish-yellow solution<br>Particulates observed<br>Clear solution | Slightly greenish-yellow solution<br>Particulates observed<br>Clear solution |
| Assay | 7.6-8.4 mg/mL | 7.9 mg/ml | 8.0 mg/ml | 7.9 mg/ml |
| Impurities and Degradation Products | Unspecified and Unidentified Impurities: ≤0.1% (w/w) | RRT 0.76 <LOQ<br>RRT 0.80 <LOQ<br>Imatinib EP Impurity C: 0.03%<br>RRT 0.92 <LOQ<br>Imatinib Para-PPA Impurity: <LOQ<br>RRT 1.05: 0.01%<br>RRT 1.06: 0.02%<br>RRT 1.09 <LOD<br>RRT 1.107 <LOQ<br>RRT 1.114: 0.02%<br>RRT 1.14: 0.01%<br>RRT 1.147: 0.01%<br>RRT 1.155: 0.03%<br>RRT 1.167: 0.01%<br>RRT 1.174: 0.01% | RRT 0.76 <LOQ<br>RRT 0.80 <LOQ<br>Imatinib EP Impurity C: 0.01%<br>RRT 0.92 <LOQ<br>Imatinib Para-PPA Impurity: 0.01%<br>RRT 0.98 <LOD<br>RRT 0.99 <LOD<br>RRT 1.03: 0.02%<br>RRT 1.05: 0.01%<br>RRT 1.06: 0 01%<br>RRT 1.12: 0.01% | RRT 0.76 <LOQ<br>RRT 0.80 <LOQ<br>RRT 0.81 <LOD<br>RRT 0.87 <LOD<br>Imatinib EP Impurity C: 0.02%<br>RRT 0.92 <LOQ<br>Imatinib Para-PPA Impurity: <LOQ<br>RRT 1.03: 0.03%<br>RRT 1.04. 0.02%<br>RRT 1.06: 0.01%<br>RRT 1.12: 0.02% |
| | Specified Impurities:<br>Impurity A: NMT 0.03% (w/w) | ND | ND | ND |
| | Imatinib EP Impurity F: NMT 0.03% (w/w) | ND | ND | ND |
| | Imatinib EP Impurity J: NMT 0.2% (w/w) | 0.03% | 0.04% | 0.04% |
| | RRT 0.66: NMT 0.2% (w/w) | ND | ND | ND |
| | RRT 0.71: NMT 0.2% (w/w) | ND | ND | <LOD |
| | Total Impurities: ≤2.0% (w/w) | 0.19% | 0.10% | 0.13% |
| pH | 4.5-5.5 | 5.1 | 5.1 | 5.1 |
| Osmolality | 270-330 mOsmol/kg | 302 mOsmol/kg | 304 mOsmol/kg | 305 mOsmol/kg |
| Particulate Contamination | ≥10 μm: NMT 6000 particles/vial<br>≥25 μm: NMT 600 particles/vial | ≥10 μm: 65 particles/vial<br>≥25 μm: 17 particles/vial | ≥10 μm: 13 particles/vial<br>≥25 μm: 0 particles/vial | ≥10 μm: 13 particles/vial<br>≥25 μm: 0 particles/vial |

Note:
ND = Not Detected
LOD for Imatinib EP Impurity F is 0.0016% (w/w)
LOQ for Imatinib EP Impurity F is 0.005% (w/w)
LOD is 0.0033% w/w for all other Specified Impurities
LOQ is 0.010% w/w for all other Specified Impurities
For all Unspecified and Unidentified Impurities LOD is 0.0033% w/w and LOQ is 0.010% w/w

TABLE 5-3

Stability Data (laboratory batch) from storage at 40° C./75% RH (stored inverted)

| Test | Specification | Initial | 1 month | 3 months |
|---|---|---|---|---|
| Appearance | Colorless to slightly greenish-yellow solution<br>Solution free of visible particles<br>Clear solution | Slightly greenish-yellow solution<br>Particulates observed<br>Clear solution | Slightly greenish-yellow solution<br>Particulates observed<br>Clear solution | Slightly greenish-yellow solution<br>Particulates observed<br>Clear solution |
| Assay | 7.6-8.4 mg/mL | 7.9 mg/ml | 7.9 mg/ml | 7.9 mg/ml |
| Impurities and Degradation Products | Unspecified and Unidentified Impurities: ≤0.1% (w/w) | RRT 0.76 <LOQ<br>RRT 0.80 <LOQ<br>Imatinib EP Impurity C: 0.03%<br>RRT 0.92 <LOQ<br>Imatinib Para-PPA Impurity: <LOQ<br>RRT 1.05: 0.01%<br>RRT 1.06: 0.02%<br>RRT 1.09 <LOD<br>RRT 1.107 <LOQ<br>RRT 1.114: 0.02%<br>RRT 1.14: 0.01%<br>RRT 1.147: 0.01%<br>RRT 1.155: 0.03%<br>RRT 1.167: 0.01%<br>RRT 1.174: 0.01% | RRT 0.76 <LOQ<br>RRT 0.80 <LOQ<br>Imatinib EP Impurity C: 0.01%<br>RRT 0.92 <LOQ<br>Imatinib Para-PPA Impurity: 0.01%<br>RRT 0.98 <LOD<br>RRT 0.99 <LOD<br>RRT 1.03: 0.01%<br>RRT 1.04: 0.02%<br>RRT 1.06: 0 01%<br>RRT 1.12: 0.01% | RRT 0.76 <LOQ<br>RRT 0.80 <LOQ<br>RRT 0.81 <LOD<br>RRT 0.87 <LOD<br>Imatinib EP Impurity C: 0.02%<br>RRT 0.92 <LOQ<br>Imatinib Para-PPA Impurity: <LOQ<br>RRT 1.03: 0.02%<br>RRT 1.04. 0.02%<br>RRT 1.06: 0.01%<br>RRT 1.12: 0.02% |

TABLE 5-3-continued

Stability Data (laboratory batch) from storage at 40° C./75% RH (stored inverted)

| Test | Specification | Initial | 1 month | 3 months |
|---|---|---|---|---|
| | Specified Impurities: | | | |
| | Impurity A: NMT 0.03% (w/w) | ND | ND | ND |
| | Imatinib EP Impurity F: NMT 0.03% (w/w) | ND | ND | <LOD |
| | Imatinib EP Impurity J: NMT 0.2% (w/w) | 0.03% | 0.04% | 0.04% |
| | RRT 0.66: NMT 0.2% (w/w) | ND | ND | ND |
| | RRT 0.71: NMT 0.2% (w/w) | ND | ND | <LOD |
| | Total Impurities: ≤2.0% (w/w) | 0.19% | 0.10% | 0.10% |
| pH | 4.5-5.5 | 5.1 | 5.1 | 5.1 |
| Osmolality | 270-330 mOsmol/kg | 302 mOsmol/kg | 304 mOsmol/kg | 303 mOsmol/kg |
| Particulate Contamination | ≥10 μm: NMT 6000 particles/vial ≥25 μm : NMT 600 particles/vial | ≥10 μm: 65 particles/vial ≥25 μm: 17 particles/vial | ≥10 μm: 2 particles/vial ≥25 μm: 0 particles/vial | ≥10 μm: 20 particles/vial ≥25 μm: 6 particles/vial |

Note:
ND = Not Detected
LOD for Imatinib EP Impurity F is 0.0016% (w/w)
LOQ for Imatinib EP Impurity F is 0.005% (w/w)
LOD is 0.0033% w/w for all other Specified Impurities
LOQ is 0.010% w/w for all other Specified Impurities
For all Unspecified and Unidentified Impurities LOD is 0.0033% w/w and LOQ is 0.010% w/w

TABLE 5-4

Stability Data (clinical batch) from storage at 25° C. /60% RH (stored inverted)

| Test | Specification | Initial | 1 month |
|---|---|---|---|
| Appearance | Colorless to slightly greenish-yellow solution Solution free of visible particles Clear solution | Slightly greenish-yellow solution Free of visible particles Clear solution | Slightly greenish-yellow solution Free of visible particles Clear solution |
| Assay | 7.6-8.4 mg/mL | 8.0 mg/ml | 8.0 mg/ml |
| Impurities and Degradation Products | Unspecified and Unidentified Impurities: ≤0.1% (w/w) | RRT 0.22 <LOD RRT 0.79: 0.01% Imatinib EP Impurity C: 0.01% RRT 0.88 <LOD Imatinib Para-PPA Impurity: <LOD RRT 1.05: 0.01% RRT 1.06 <LOD RRT 1.12: 0.03% RRT 1.20: 0 01% | RRT 1.04:0.015% RRT 1.06 <LOQ RRT 1.12: 0.034% RRT 1.22 <LOQ |
| | Specified Impurities: | | |
| | Impurity A: NMT 0.03% (w/w) | <LOD | ND |
| | Imatinib HP Impurity F: NMT 0 03% (w/w) | ND | ND |
| | Imatinib EP Impurity J: NMT 0 2% (w/w) | <LOD | 0.012% |
| | RRT 0.66: NMT 0.2% (w/w) | ND | ND |
| | RRT 0.71: NMT 0.2% (w/w) | <LOD | ND |
| | Total Impurities: ≤2.0% (w/w) | 0.10% | 0.10% |
| pH | 4.5-5.5 | 5.1 | 5.1 |
| Osmolality | 270-330 mOsmol/kg | 305 mOsmol/kg | 309 mOsmol/kg |
| Particulate Contamination | ≥10 μm: NMT 6000 particles/vial ≥25 μm : NMT 600 particles/vial | ≥10 μm: 6 particles/vial ≥25 μm: 2 particles/vial | ≥10 μm: 15 particles/vial ≥25 μm: 0 particles/vial |

Note:
ND = Not Detected
LOD for Imatinib EP Impurity F is 0.0016% (w/w)
LOQ for Imatinib EP Impurity F is 0.005% (w/w)
LOD is 0.0033% w/w for all other Specified Impurities
LOQ is 0.010% w/w for all other Specified Impurities
For all Unspecified and Unidentified Impurities LOD is 0.0033% w/w and LOQ is 0.010% w/w

TABLE 5-5

| Test | Specification | Initial | 1 month |
|---|---|---|---|
| Appearance | Colorless to slightly greenish-yellow solution | Slightly greenish-yellow solution | Slightly greenish-yellow solution |
| | Solution free of visible particles | Free of visible particles | Free of visible particles |
| | Clear solution | Clear solution | Clear solution |
| Assay | 7.6-8.4 mg/mL | 8.0 mg/ml | 8.0 mg/ml |
| Impurities and Degradation Products | Unspecified and Unidentified Impurities: ≤0.1% (w/w) | RRT 0.22 <LOD<br>RRT 0.79: 0.01%<br>Imatinib EP Impurity C: 0.01%<br>RRT 0.88 <LOD<br>Imatinib Para-PPA Impurity: <LOD<br>RRT 1.05: 0.01%<br>RRT 1.06 <LOD<br>RRT 1.12: 0.03%<br>RRT 1.20: 0 01% | RRT 1.04: 0.024%<br>RRT 1.05 <LOQ<br>RRT 1.12: 0.034%<br>RRT 1.22 <LOQ |
| | Specified Impurities: | | |
| | Impurity A: NMT 0.03% (w/w) | <LOD | ND |
| | Imatinib EP Impurity F: NMT 0.03% (w/w) | ND | ND |
| | Imatinib EP Impurity J: NMT 0.2% (w/w) | <LOD | 0.012% |
| | RRT 0.66: NMT 0.2% (w/w) | ND | ND |
| | RRT 0.71: NMT 0.2% (w/w) | <LOD | ND |
| | Total Impurities: ≤2.0% (w/w) | 0.19% | 0.10% |
| pH | 4.5-5.5 | 5.1 | 5.1 |
| Osmolality | 270-330 mOsmol/kg | 305 mOsmol/kg | 306 mOsmol/kg |
| Particulate Contamination | ≥10 μm: NMT 6000 particles/vial<br>≥25 μm : NMT 600 particles/vial | ≥10 μm: 6 particles/vial<br>≥25 μm: 2 particles/vial | ≥10 μm: 15 particles/vial<br>≥25 μm: 0 particles/vial |

Note:
ND = Not Detected
LOD for Imatinib EP Impurity F is 0.0016% (w/w)
LOQ for Imatinib EP Impurity F is 0.005% (w/w)
LOD is 0.0033% w/w for all other Specified Impurities
LOQ is 0.010% w.w for all other Specified Impurities
For all Unspecified and Unidentified Impurities LOD is 0.0033% w/w and LOQ is 0.010% w/w

EQUIVALENTS

It is to be understood that the disclosure can be embodied in other specific forms without departing from the spirit or essential characteristics thereof. The foregoing embodiments and disclosures are therefore to be considered in all respects illustrative rather than limiting on the disclosure described herein. Scope of the disclosure is thus indicated by the appended claims rather than by the foregoing description, and all changes that come within the meaning and range of equivalency of the claims are intended to be embraced therein.

The invention claimed is:

1. A pharmaceutical formulation for intravenous administration, comprising:
   a. Compound A:

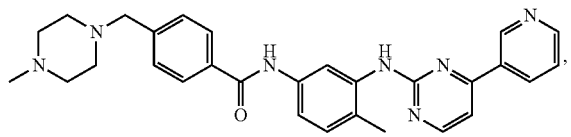 [SMILES: Cc1ccc(NC(=O)c2ccc(CN3CCN(C)CC3)cc2)cc1Nc1nccc(-c2cccnc2)n1]

or a pharmaceutically acceptable salt thereof, wherein Compound A is present in the amount from about 7.2 mg/mL to about 8.8 mg/mL;
   b. a tonicity adjusting agent selected from a polyhydric alcohol, a salt, a saccharide, and a combination thereof;
   c. a buffering agent selected from a phosphate buffer, a borate buffer, a citrate buffer, a tartrate buffer, an acetate buffer, an amino acid, and a combination thereof; and
   d. a pH adjusting agent.

2. The pharmaceutical formulation of claim 1, wherein Compound A is present in the amount of about 8.0 mg/mL.

3. The pharmaceutical formulation of claim 1, comprising a mesylate salt of Compound A:

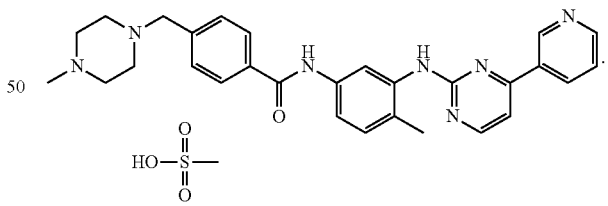

4. The pharmaceutical formulation of claim 1, wherein the tonicity adjusting agent is selected from glycerol, NaCl, and a combination thereof.

5. The pharmaceutical formulation of claim 4, wherein the tonicity adjusting agent is glycerol.

6. The pharmaceutical formulation of claim 5, comprising from about 1.5% (v/v) to about 2.5% (v/v) glycerol.

7. The pharmaceutical formulation of claim 1, wherein the buffering agent is an acetate buffer.

8. The pharmaceutical formulation of claim 7, comprising from about 0.005 M to about 0.015 M acetate buffer.

9. The pharmaceutical formulation of claim 1, comprising from about 7.2 mg/mL to about 8.8 mg/mL Compound A; from about 1.5% (v/v) to about 2.5% (v/v) glycerol; and from about 0.005 M to about 0.015 M acetate buffer.

10. The pharmaceutical formulation of claim 1, wherein the tonicity of the pharmaceutical formulation is about 300 mOsm.

11. The pharmaceutical formulation of claim 1, wherein the pH of the pharmaceutical formulation is 5±0.2.

12. The pharmaceutical formulation of claim 1, wherein the pharmaceutical formulation comprises:

less than 0.05% (w/w) of Impurity A:

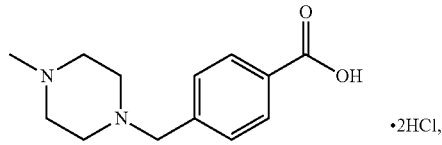 [SMILES: CN1CCN(Cc2ccc(C(=O)O)cc2)CC1]

·2HCl, and/or less than 0.05% (w/w) of Impurity F:

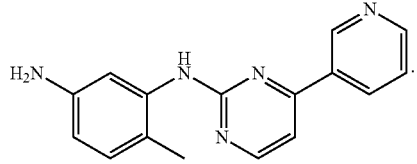 [SMILES: Cc1ccc(N)cc1Nc1nccc(-c2cccnc2)n1]

13. The pharmaceutical formulation of claim 1, wherein the pharmaceutical formulation comprises:

less than 0.5% (w/w) of Impurity B:

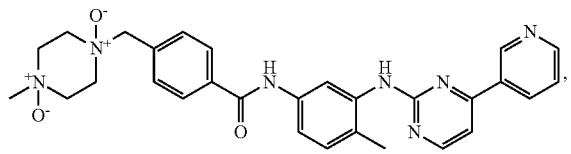 [SMILES: Cc1ccc(NC(=O)c2ccc(C[N+]3([O-])CC[N+](C)([O-])CC3)cc2)cc1Nc1nccc(-c2cccnc2)n1]

less than 0.5% (w/w) of Impurity C:

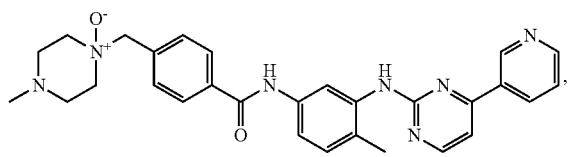 [SMILES: Cc1ccc(NC(=O)c2ccc(C[N+]3([O-])CCN(C)CC3)cc2)cc1Nc1nccc(-c2cccnc2)n1]

and/or less than 0.5% (w/w) of Impurity J:

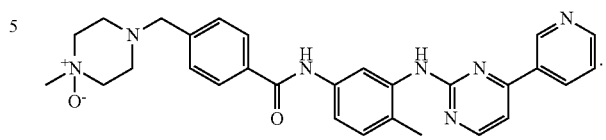

14. The pharmaceutical formulation of claim 1, wherein the pharmaceutical formulation comprises no more than 2% (w/w) of Impurity A

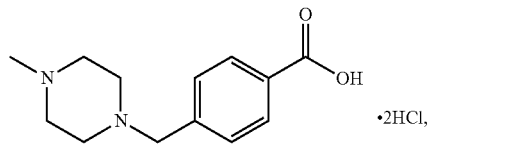

·2HCl,

Impurity B

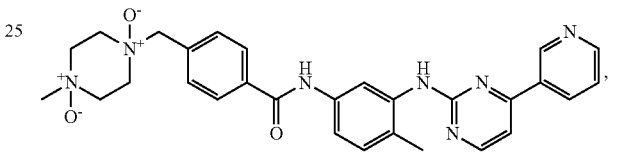

Impurity C

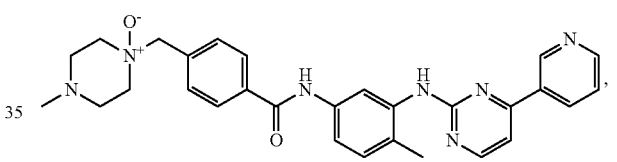

Impurity F

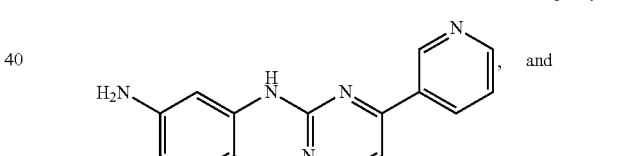

and

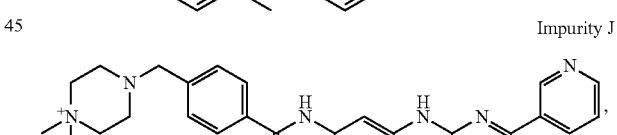

Impurity J

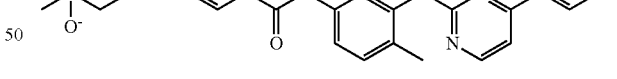

in total.

15. A method of treating acute respiratory distress syndrome (ARDS) in a subject in need thereof, comprising administering to the subject a therapeutically effective amount of the pharmaceutical formulation of claim 1.

16. The method of claim 15, wherein the pharmaceutical formulation is administered through intravenous infusion.

17. The method of claim 15, wherein the therapeutically effective amount is between about 100 mg and about 500 mg per day.

18. The method of claim 17, wherein the therapeutically effective amount is about 400 mg per day.

* * * * *